United States Patent
Chou et al.

(10) Patent No.: US 9,387,488 B2
(45) Date of Patent: Jul. 12, 2016

(54) MOLECULAR ENTRAPMENT AND ENRICHMENT

(71) Applicant: Academia Sinica, Taipei (TW)

(72) Inventors: Chia-Fu Chou, Taipei (TW); Kuo-Tang Liao, Taichung (TW)

(73) Assignee: ACADEMIA SINICA, Taipei (TW)

( * ) Notice: Subject to any disclaimer, the term of this patent is extended or adjusted under 35 U.S.C. 154(b) by 343 days.

(21) Appl. No.: 13/675,735

(22) Filed: Nov. 13, 2012

(65) Prior Publication Data
US 2014/0131204 A1     May 15, 2014

(51) Int. Cl.
| G01N 27/447 | (2006.01) |
| B03C 5/00 | (2006.01) |
| B03C 5/02 | (2006.01) |
| B01L 3/00 | (2006.01) |
| G01N 15/00 | (2006.01) |
| G01N 15/06 | (2006.01) |

(52) U.S. Cl.
CPC ........... *B03C 5/005* (2013.01); *B01L 3/502761* (2013.01); *B03C 5/026* (2013.01); *B01L 2200/0652* (2013.01); *B01L 2300/0816* (2013.01); *B01L 2300/0896* (2013.01); *B01L 2400/0424* (2013.01); *B01L 2400/086* (2013.01); *B03C 2201/26* (2013.01); *G01N 15/06* (2013.01); *G01N 15/0612* (2013.01); *G01N 27/44713* (2013.01); *G01N 2015/0065* (2013.01)

(58) Field of Classification Search
CPC ...... G01N 27/447; G01N 27/221; B03C 5/00; B01D 57/02
USPC ....................... 204/452, 463; 422/68.1, 82.01; 435/287.1
See application file for complete search history.

(56) References Cited

U.S. PATENT DOCUMENTS

| 6,824,664 B1 * | 11/2004 | Austin et al. ................. 204/643 |
| 2005/0161326 A1 * | 7/2005 | Morita et al. ................. 204/450 |
| 2006/0063273 A1 * | 3/2006 | Asogawa et al. ............. 436/180 |
| 2006/0180469 A1 * | 8/2006 | Han et al. ..................... 204/601 |
| 2007/0090026 A1 * | 4/2007 | Han et al. ......................... 209/2 |
| 2007/0105206 A1 * | 5/2007 | Lu et al. ..................... 435/173.6 |

(Continued)

FOREIGN PATENT DOCUMENTS

WO          WO 01/37958       *   5/2001

OTHER PUBLICATIONS

Khang, Electrophoresis 2006, 27, 694-702.*

(Continued)

*Primary Examiner* — Jennifer Dieterle
(74) *Attorney, Agent, or Firm* — Perkins Coie LLP

(57) ABSTRACT

Methods, structures, devices and systems are disclosed for rapid enrichment and mass transport of biomolecules (e.g., such as proteins) or other small molecules and particles using electrodeless dielectrophoresis (eDEP). In one aspect, a device to aggregate molecules includes a substrate that is electrically insulating, an electrically insulative material formed on the substrate and structured to form a channel to carry an electrically conducting fluid containing particles, a constriction structure formed of the electrically insulative material and located in the channel to narrow a channel dimension and forming an opening with a size in the nanometer range, and a circuit coupled to the substrate to apply an ac electric field and a dc bias electric field along the channel, in which the constriction structure is structured to magnify the applied ac electric field to produce forces that operate collectively to aggregate the particles.

42 Claims, 12 Drawing Sheets

(56) References Cited

U.S. PATENT DOCUMENTS

| | | | |
|---|---|---|---|
| 2008/0067068 A1* | 3/2008 | Li ................................ | 204/451 |
| 2009/0214392 A1* | 8/2009 | Kameoka .......... | B01L 3/502761 422/400 |
| 2010/0183634 A1* | 7/2010 | Luo et al. ................... | 424/178.1 |

OTHER PUBLICATIONS

Zhang, Bioparticle Separation in Microfluidic Devices, 2009.*
Sridharan, Electrophoresis 2011, 32, 2274-2281.*
Hawkins, Electrophoresis 2010, 31, 3622-3633.*
Liao, Electrophoresis 2012, 33, 1958-1966.*
Chou et al., 2003, Electrodeless dielectrophoresis for micro total analysis system.*
Chou et al., 2002, Biophysical Journal 83(4) 2170-2179.*
Armenia, J.M. et al., "Coupled affinity-hydrophobic monolithic column for on-line removal of immunoglobulin G, preconcentration of low abundance proteins and separation by capillary zone electrophoresis," Journal of Chromatography A, 1148:115-122, Mar. 2007.
Cheetham, M.R. et al., "Concentrating membrane proteins using asymmetric traps and AC electric fields," Journal of the American Chemical Society, 133:6521-6524, Apr. 2011.
Chou, C.F. et al., "Electrodeless dielectrophoresis for micro total analysis systems," IEEE Engineering in Medicine and Biology Magazine, 22(6):62-67, Nov./Dec. 2003.
Chou, C.F. et al., "Electrodeless dielectrophoresis of single- and double-stranded DNA," Biophysical Journal, 83:2170-2179, Oct. 2002.
Ge, Z. et al., "Towards high concentration enhancement of microfluidic temperature gradient focusing of sample solutes using combined AC and DC field induced Joule heating," Lab Chip, 11:1396-1402, Jan. 2011.
Greenlee, R.D. et al., "Protein focusing in a conductivity gradient," Biotechnology Progress, 14(2):300-309, Jan. 1998.
Huang, H. et al., "On-line isotachophoretic preconcentration and gel electrophoretic separation of sodium dodecyl sulfate-proteins on a microchip," Electrophoresis, 26(11):2254-2260, Jun. 2005.
Huang, K.D. et al., "A nanochannel-based concentrator utilizing the concentration polarization effect," Electrophoresis, 29(24):4862-4870, Dec. 2008.
Inglis, D.W. et al., "Simultaneous concentration and separation of proteins in a nanochannel," Angewandte Chemie International Edition, 50(33):7546-7550, Aug. 2011.
Kim, S.M. et al., "Electrokinetic protein preconcentration using a simple glass/poly(dimethylsiloxane) microfluidic chip," Analytical Chemistry, 78(14):4779-4785, May 2006.
Lee, J.H. et al., "Multiplexed proteomic sample preconcentration device using surface-patterned ion-selective membrane," Lab Chip, 8(4):596-601, Apr. 2008.
Matsui, T. et al., "Temperature gradient focusing in a PDMS/glass hybrid microfluidic chip," Electrophoresis, 28(24):4606-4611, Dec. 2007.
Nie, F.Q. et al., "Micro-flow injection analysis system: on-chip sample preconcentration, injection and delivery using coupled monolithic electroosmotic pumps," Lab Chip, 7:1597-1599, Aug. 2007.
Ross, D. et al., "Microfluidic temperature gradient focusing," Analytical Chemistry, 74:2556-2564, Apr. 2002.
Swami, N. et al., "Enhancing DNA hybridization kinetics through constriction-based dielectrophoresis," Lab Chip, 9:3212-3220, Sep. 2009.
Wang, Y.C. et al., "Pre-binding dynamic range and sensitivity enhancement for immuno-sensors using nanofluidic preconcentrator," Lab Chip, 8(3):392-394, Jan. 2008.
Wu, D. et al., "High speed nanofluidic protein accumulator," Lab Chip, 9:1890-1896, Mar. 2009.
Chaurey, Vasudha et al., "Floating-electrode enhanced constriction dielectrophoresis for biomolecular trappin in physiological media of high conductivity", Biomicrofluidics 6, 012806, 2012, 15 pages.
Clarke, Richard W., "Trapping of Proteins under Physiological Conditions in a Nanopipette", Angew. Chem. Int. Ed. 2005, 44, pp. 3747-3750.
Lapizco-Encinas, Blanco H. et al., "Protein manipulation with insulator-based dielectrophoresis and direct current electric fields", Journal of Chromatography A, 1206, 2008, pp. 45-51.
Liao, Kuo-Tang et al., "Ultrafast Protein Preconcentration by Nanoscale Molecular Traps", Nov. 2009, pp. 204-206.

* cited by examiner

MOLECULAR ENTRAPMENT AND ENRICHMENT

TECHNICAL FIELD

This patent document relates to biological sensors and analytical devices.

BACKGROUND

A biological sensor or biosensor is an analytical tool that can detect a chemical, substance, or organism using a biologically sensitive component coupled with a transducing element to convert a detection event into a signal for processing and/or display. Biosensors can use biological materials as the biologically sensitive component, e.g., such as biomolecules including enzymes, antibodies, aptamers, peptides, nucleic acids, etc., or small molecules such as carbohydrates, as well as virus and living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by a suitable transduction mechanism, for example, electrical, magnetic, mechanical, physicochemical, electrochemical, optical, piezoelectric, or others.

SUMMARY

Techniques, systems, and devices are described for rapid enrichment and mass transport of biomolecules or other small molecules and particles using electrodeless dielectrophoresis (eDEP).

In one aspect of the disclosed technology, a device to aggregate particles in a fluid includes a substrate that is electrically insulating, an electrically insulative material formed on the substrate and structured to form a channel to carry an electrically conducting fluid containing particles, a constriction structure formed of the electrically insulative material and located in the channel to narrow a channel dimension and forming an opening with a size in the nanometer range, and a circuit coupled to the substrate to apply an ac electric field and a dc bias electric field along the channel, in which the constriction structure is structured to magnify the applied ac electric field to produce a negative dielectrophoretic force ($F_{NDEP}$) in a direction away from the opening to combine with an electroosmotic force ($F_{EO}$) that is caused by the applied ac electric field with the dc bias to be in the direction away from the opening to counter an electrophoretic force ($F_{EP}$) in a direction toward the opening so that the $F_{NDEP}$, $F_{EO}$, and $F_{EP}$ operate collectively to aggregate the particles in an adjacent region on a side of the opening.

Implementations of the device can optionally include one or more of the following features. The circuit of the device can include a gating electrode configured outside of an insulative layer provided by at least one of the channel or the substrate and located along the channel on a side of the constriction structure to provide an electrical charge used to affect the $F_{EO}$. The device can further include a sensor located along the channel to detect a parameter of the aggregated particles. In some implementations, the sensor can include an optical micrograph imager that detects an illumination intensity of the aggregated particles. In some implementations, the sensor can include at least one of an electrical sensor, an electrochemical sensor, a mechanical sensor, or a magnetic sensor. The device can further include a first feeder channel and a second feeder channel having a channel width in a micrometer range or greater and formed of the electrically insulative material structured to carry the electrically conducting fluid, in which the channel is located between and connected to the first feeder channel and the second feeder channel. The device can further include fluidic reservoirs located along the first feeder channel and the second feeder channel and electrode terminals configured within the fluidic reservoirs and in contact with the fluid, in which the ac electric field and the dc bias is applied along the channel across the electrode terminals.

In another aspect of the disclosed technology, a method to aggregate particles in a fluid includes receiving an electrically conducting fluid containing particles in a channel formed of an electrically insulative material and having a constriction structure narrowing a channel dimension to form an opening with a size in the nanometer range, selecting a frequency and magnitude of an ac electric field to be applied along the channel, selecting a bias magnitude of a dc electrical signal to be applied along the channel, and applying the ac electric field and the dc bias along the channel to aggregate the particles in a region near the opening, in which the selecting the frequency of the ac electric field determines if the constriction structure magnifies the applied ac electric field to produce a $F_{NDEP}$ in a direction away from the opening or a $F_{PDEP}$ in a direction toward the opening, and in which the selecting the bias magnitude of the dc electric signal to a nonzero value controls an electrophoretic force.

Implementations of the method can optionally include one or more of the following features. The method can further include selecting electrical parameters to separate a first type of particles from a second type of particles based on differences in polarizability and electrokinetic mobility of the first and second type of particles. The method can further include detecting a parameter of the aggregated particles using a sensor configured along the channel, e.g., in which the sensor includes at least one of an electrical sensor, an electrochemical sensor, a mechanical sensor, or a magnetic sensor. For example, the detecting can include acquiring an optical micrograph data including illumination intensity of the aggregated particles.

In another aspect of the disclosed technology, a system to characterize particles includes an electrodeless dielectrophoresis chip, an electrical energy source, and a characterization unit. The electrodeless dielectrophoresis chip includes a substrate that is electrically insulating and structured to define a channel to carry an electrically conducting fluid containing particles, a constriction structure of an electrically insulative material configured in the channel to narrow a dimension of the channel and forming an opening with a size in the nanometer range, two microchannels formed of the electrically insulative material and having a channel width in a micrometer range or greater, in which the channel is located between and connected to the two microchannels, and fluidic reservoirs located along the two microchannels. The electrical energy source generates an ac electric field with a dc bias along the channel across electrode terminals configured within the fluidic reservoirs and in contact with the fluid, in which the constriction structure magnifies the applied ac electric field to produce a negative dielectrophoretic force ($F_{NDEP}$) in a direction away from the opening, and the applied ac electric field with the dc bias produces an electroosmotic force ($F_{EO}$) in the direction away from the opening and an electrophoretic force ($F_{EP}$) in a direction toward the opening, in which the $F_{NDEP}$, $F_{EO}$, and $F_{EP}$ combine to aggregate the particles in an adjacent region on a side of the opening. The characterization unit includes a sensor positioned along the channel to detect a parameter of the aggregated particles and a processing unit to process the detected parameter as data to determine a characteristic of the particles.

Implementations of the system can optionally include one or more of the following features. The electrodeless dielectrophoresis chip of the system can further include a gating electrode configured outside of an insulative layer provided by at least one of the channel or the substrate and located along the channel on a side of the constriction structure to provide an electrical charge used to affect the $F_{EO}$.

In another aspect of the disclosed technology, a device to separate types of particles in a fluid includes a substrate that is electrically insulating, an electrically insulative material formed on the substrate and structured to form a channel to carry an electrically conducting fluid containing two or more types of particles, an array of constriction structures formed of the electrically insulative material and located in the channel to narrow a channel dimension, in which a first constriction structure of the array forms a first opening of a size smaller than that of a second opening formed by a second constriction structure of the array, the size being in the nanometer range, and a circuit coupled to the substrate to apply an ac electric field and a dc bias electric field along the channel. The first constriction structure is structured to magnify the applied ac electric field to produce a first negative dielectrophoretic force ($F_{NDEP}$) in a direction away from the first opening and the second constriction structure is structured to magnify the applied ac electric field to produce a second $F_{NDEP}$ weaker than the first $F_{NDEP}$ in the direction away from the second opening, in which the first and second $F_{NDEP}$ combine with an electroosmotic force ($F_{EO}$) that is caused by the applied ac electric field with the dc bias to be in the direction away from the opening to counter an electrophoretic force ($F_{EP}$) in a direction toward the opening, such that the first $F_{NDEP}$, $F_{EO}$, and $F_{EP}$ operate collectively to aggregate one type of particles in an adjacent region on a side of the first opening and the second $F_{NDEP}$, $F_{EO}$, and $F_{EP}$ operate collectively to aggregate another type of particles in an adjacent region on a side of the second opening.

In another aspect of the disclosed technology, a device to separate types of particles in a fluid includes a substrate that is electrically insulating, an electrically insulative material formed on the substrate and structured to form: (i) an array of channels having a channel dimension in a nanometer range and structured to carry an electrically conducting fluid containing two or more types of particles, in which a first channel of the array forms a first opening of a size smaller than that of a second opening formed by a second channel of the array and (ii) feeder channels having a channel width in a micrometer range or greater and formed of the electrically insulative material structured to carry the electrically conducting fluid, in which the array of channels is located between and connected to the feeder channels, and a circuit coupled to the substrate to apply an ac electric field and a dc bias electric field along the channel. The first channel magnifies the applied ac electric field to produce a first negative dielectrophoretic force ($F_{NDEP}$) in a direction away from the first opening and the second channel magnifies the applied ac electric field to produce a second $F_{NDEP}$ weaker than the first $F_{NDEP}$ in the direction away from the second opening, in which the first and second $F_{NDEP}$ each combine with an electroosmotic force ($F_{EO}$) that is caused by the applied ac electric field with the dc bias to be in the direction away from the corresponding opening to counter an electrophoretic force ($F_{EP}$) in a direction toward the corresponding opening, such that the first $F_{NDEP}$, $F_{EO}$, and $F_{EP}$ operate collectively to aggregate one type of particles in an adjacent region on a side of the first opening and the second $F_{NDEP}$, $F_{EO}$, and $F_{EP}$ operate collectively to aggregate another type of particles in an adjacent region on a side of the second opening.

The subject matter described in this patent document can be implemented in specific ways that provide one or more of the following features. For example, the disclosed technology can be implemented in a variety of applications including general protein assays, protein crystallization, protein precipitation, rare biomarker discovery (e.g. coupled with mass spectroscopy), early disease diagnostics, small molecules (e.g. peptides or carbohydrates) enrichment or screening. For example, implementation of the disclosed biosensor devices can provide rapid enrichment of proteins on an order of at least $10^5$-fold enrichment (e.g., in 20 seconds). Exemplary devices can include the displacement of the molecular dam away from heating spots, e.g., geometrical center of the nanoconstriction, which can alleviate Joule heating effects. The described devices can be mass produced and fabricated using low-cost materials, e.g., including polymer or plastic, and can combine other sensor modalities including molecular filtering and detection on the same device platform. For example, a biosensing element can be placed microns away from an exemplary nanoconstriction structure.

The above and other aspects and implementations of the disclosed technology are described in greater detail in the drawings, the description and the claims.

BRIEF DESCRIPTION OF THE DRAWINGS

Like reference symbols and designations in the various drawings indicate like elements.

DETAILED DESCRIPTION

Figure 1A:
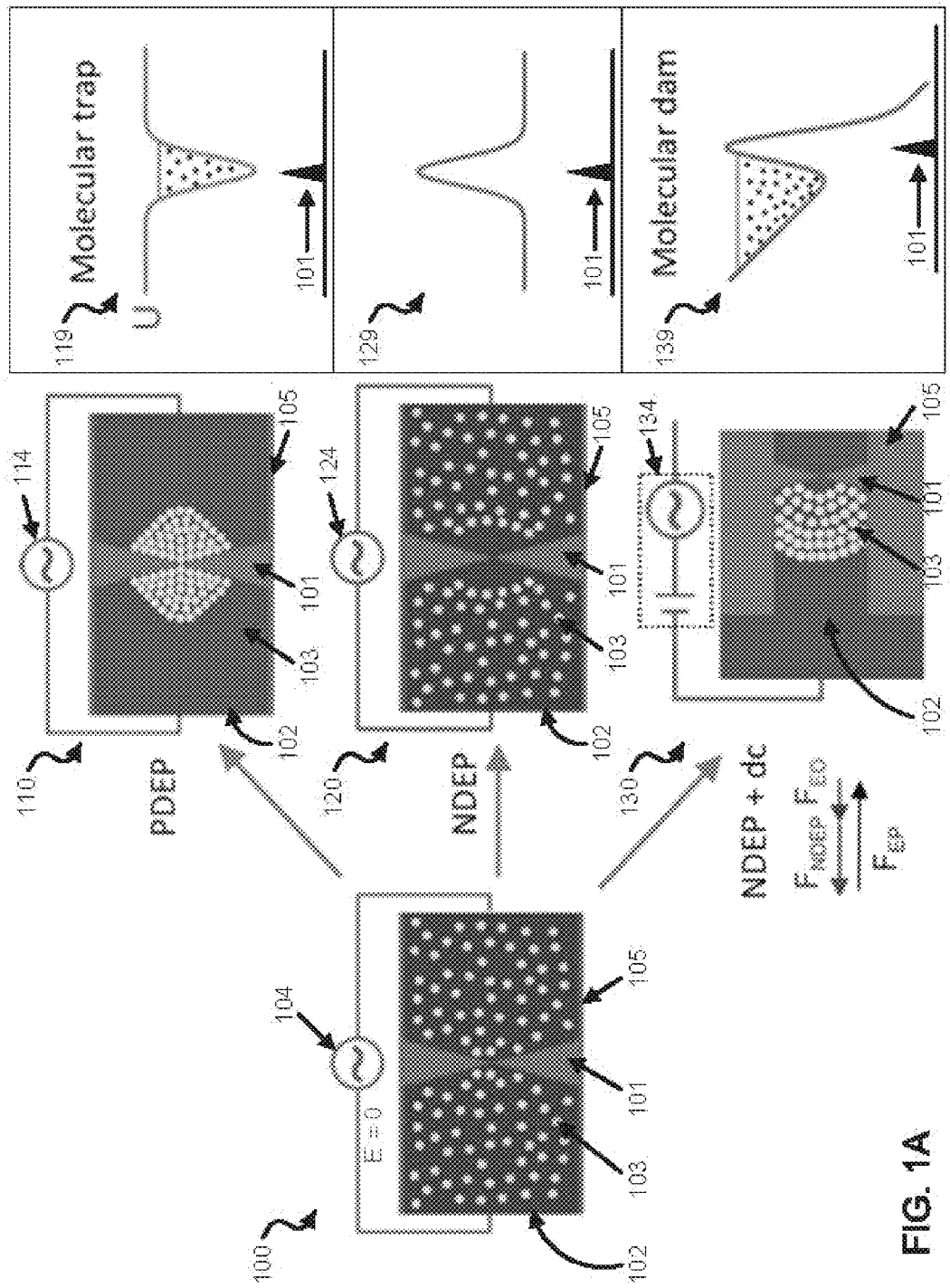
FIG. 1A shows schematic illustrations of exemplary dielectrophoretic techniques to achieve molecular trapping and molecular damming.

Mass transport has generally been recognized as a limiting factor in the sensitivity and performance of certain biosensors including various miniaturized biosensors for detecting low concentration of particles or clusters of particles such as biological or chemical particles including certain molecules or a cluster of molecules. For example, the miniaturization of biosensors can impose penalties on passive transport of biomolecules to the sensor surface, e.g., which can be due to prolonged diffusion length from the bulk liquid or in the direction of the fluidic channels. For biosensors that include biomolecules (e.g., including proteins) in low-abundance within the sample to be analyzed, sample enrichment is usually regarded as a prerequisite for high-resolution analysis due to various factors. However, chemical amplification methods may not be readily available for biomolecules in a high-resolution analysis and this lack of chemical amplification may render high-resolution analysis difficult. These exemplary limiting factors can introduce challenges in implementing the micro- or nano-scale biosensor platform, e.g., inhibiting its efficacy in applications such as early or acute disease diagnostics and biomarker discovery.

Sensing low numbers of biomarker proteins against a background of high concentration of other matrix proteins within physiologically relevant media requires effective methodologies for selective preconcentration of the biomarker in the proximity of the sensor. Such selective preconcentration can increase local concentration of the target sample for sensing by the sensor. Various preconcentration methods are available but are limited in their performance. For example, chemical methods based on antibody depletion are unable to achieve the necessary degree of preconcentration of biomarker proteins, e.g., as such biomarkers are present at $10^6$-$10^{12}$-fold lower levels than the background proteins in blood. Other examples include the use of electrokinetic methods for selective preconcentration of biomolecules. One such electrokinetic method includes dielectrophoresis, which can enable selective trapping of biomolecules and bioparticles based on the characteristic frequency response of the dielectric permittivity of the biomolecule/particle versus that of the medium. Dielectrophoretic techniques have been shown to be effective in the sorting of somewhat similar sized biological cells with differing dielectric frequency response. However, its application to smaller sized biomarkers, e.g., such as nanoscale proteins and fragments of single-stranded deoxyribonucleic acid (ssDNA), have been ineffective so far.

Dielectrophoresis (DEP) is a phenomenon in which a force is exerted on a dielectric particle (e.g., polarizable particle, including molecules and nanoscale particles) in a suspending medium when the particle is subjected to a non-uniform electric field. Although particles in general can exhibit dielectrophoretic activity in the presence of an electric field, the magnitude of the dielectrophoretic force depend on the type of medium, on certain properties of specific particles, e.g., electrical properties and shape and size, and on the frequency of the electric field exerted on the particles. For example, tuning the electric field to particular frequencies can manipulate particles with a degree of selectivity, e.g., which can result in orientation, transportation, and/or separation of the particles in the medium. For example, the non-uniform electric field can create regions within the medium of greater and lesser electric field magnitudes that can steer the particles. For example, when the permittivity of the medium is greater than that of the particle, the particle moves to regions of lesser electric field strength within the medium. Alternatively, for example, when the particle's permittivity exceeds that of the medium, the particle moves to regions of stronger electric field strength.

The dielectrophoretic force (e.g., a translational force) can be represented as:

$$F_{DEP} = 2\pi r^3 \epsilon_m Re[K(\omega)] \nabla E^2 \qquad (1)$$

where r is the radius of the particle, $\epsilon_m$ is the absolute permittivity of the suspending medium, E is the amplitude of the applied field (e.g., root-mean-squared E in the case for an ac field), and $Re[K(\omega)]$ represents the real part of the Clausius-Mossotti (CM) factor, which can be represented by:

$$K(\omega) = (\epsilon_p^* - \epsilon_m^*)/(\epsilon_p^* + 2\epsilon_m) \qquad (2)$$

where $\epsilon_m^*$ and $\epsilon_p^*$ are the complex permittivities of the medium and particle respectively, and ($\epsilon^* = \epsilon - j\sigma/\omega$), in which $\sigma$ is the conductivity, $\epsilon$ is the permittivity, and $\omega$ is the angular frequency. The CM factor represents the frequency-dependent dielectric contrast between the particle and the suspending medium in an external driving field. The CM factor determines if the particle transport is either towards (attracted) the high field gradient region of the fluidic channel (e.g., when $Re[K(\omega)]>0$), correspondingly by positive dielectrophoresis (PDEP), or if the particle transport is away (repelled) from the high field gradient region of the fluidic channel (e.g., when $Re[K(\omega)]<0$), correspondingly by negative dielectrophoresis (NDEP).

Since $F_{DEP}$ is proportional to the size of the molecules ($\sim r^3$), it can be difficult in various applications to generate a sufficient dielectrophoretic force to enrich small biomolecules such as proteins by DEP (e.g., proteins can be a few nanometers in size, in the 10's-100 kDa). Also, proteins exhibit a small CM factor due to their low polarizability. To overcome this limitation and entrap and enrich small biomolecules, the disclosed technology creates a highly focused field and field gradient to increase $F_{DEP}$ by engineering the $\nabla E^2$ (or $E \cdot \nabla E$) term in Eq. (1).

Techniques, systems, and devices are described herein for rapid enrichment and mass transport of biomolecules, e.g., including proteins, or other small molecules and particles using electrodeless dielectrophoresis (eDEP).

In one aspect, the disclosed technology can include a biosensor and actuator device having fluidic channels that include nanoscale structures of an electrically insulating material (e.g., referred to as nanoconstrictions) formed on a substrate that can function as molecular dams (as well as molecular traps) to enhance mass transport for protein enrichment in an electrically conducting fluid containing particles carried by the channels using electrodeless dielectrophoresis. Particle aggregation and separation, e.g., including protein enrichment when the particles include proteins, can be implemented under physiological buffer conditions using the disclosed device. For example, since the size or the polarizability of proteins is much smaller than those of DNA or cells, entrapping and/or enriching proteins can require an ultrahigh field gradient. The nanoconstrictions can be embedded in a fluidic channel of the device to serve as a field-focusing lens to enhance a local electric field by several orders of magnitude (e.g., $10^5$-fold) over the applied non-uniform ac field and associated field gradient. The enhanced field and field gradient can compensate for the small size and low CM factor of proteins and other small biomolecules to overcome their large diffusion coefficient. These high fields and field gradients can be generated using the nanoconstriction, e.g., rather than using electrodes positioned within the channel, thereby producing a dielectrophoretic effect without electrodes, or electrodeless dielectrophoresis. The exemplary dielectric nanoconstriction can be configured in the channel to narrow the channel width to an opening which can be in the tens of nanometers in size (e.g., 30 nm in size).

In one embodiment of the biosensor and actuator device for protein entrapment and enrichment, one or more nanoconstrictions are provided in a nanofluidic channel (nanochannels) with interconnections to microfluidic channels, e.g., for sample handling. A non-uniform ac electric field is applied with a dc bias along the nanochannel including the nanoconstrictions to produce forces that aggregate and contain the proteins from the fluid within a region adjacent to a nanoconstriction location. The forces at a nanoconstruction location include (1) NDEP forces generated by the highly focused fields rendered at nanoconstrictions by controlling the frequency of an applied non-uniform ac electric field, (2) electrophoretic forces generated by the electric field produced along the channel by the applied dc bias, and (3) electroosmotic forces that are produced by Coulomb effects induced by the electric field on net mobile electric charge in the fluid solution (e.g., because the chemical equilibrium between a solid surface (e.g., the substrate) and an electrolyte solution (e.g., the fluid) leads to the interface acquiring a net fixed electrical charge, a layer of mobile ions (the double layer or Debye layer) forms in the region near the interface, in which the net charge in the Debye layer is induced by the electric field to move by the resulting Coulomb force). For example, the net transport from electrophoresis (EP) is opposed by NDEP and electroosmosis (EO) through a force balance condition, $F_{EP}=F_{EO}+F_{NDEP}$. This effect of the force balance condition can enrich proteins away from the nanostructured points, referred to as a molecular dam. Implementations of the device can include applying the ac field (e.g., ac field amplitude>>dc bias) to impose a strong NDEP force at the nanoconstriction(s) to aggregate and maintain the biomolecules in a region adjacent to the nanoconstriction opening.

In implementations, the described device to aggregate particles in an electrically conducing fluid can be configured to include a substrate that is electrically insulating, an electrically insulative material formed on the substrate and structured to form a channel to carry an electrically conducting fluid containing particles, a constriction structure formed of the electrically insulative material and located in the channel to narrow a channel dimension and forming an opening with a size in the nanometer range, and a circuit coupled to the substrate to apply an ac electric field and a dc bias electric field along the channel, in which the constriction structure is structured to magnify the applied ac electric field to produce a negative dielectrophoretic force ($F_{NDEP}$) in a direction away from the opening to combine with an electroosmotic force ($F_{EO}$) that is caused by the applied ac electric field with the dc bias to be in the direction away from the opening to counter an electrophoretic force ($F_{EP}$) in a direction toward the opening so that the $F_{NDEP}$, $F_{EO}$, and $F_{EP}$ operate collectively to aggregate the particles in an adjacent region on a side of the opening.

FIG. 1A shows schematic illustrations of an exemplary dielectrophoretic device 100 to achieve molecular trapping and molecular damming of biomolecules (e.g., proteins) in a fluidic channel. The device 100 of FIG. 1A includes an electrically insulating substrate on which various components are formed. As shown, a channel 102 is formed on the substrate to carry a fluid and includes a constriction structure 101 located within the channel carrying a fluid containing molecules 103 prior to the application of an electric field produced by an electrical energy source 104 (e.g., such as a function generator). The exemplary molecules 103 can include, but are not limited to, proteins, nucleic acids (DNA or RNA), peptides, or carbohydrates. In some implementations, the channel 102 carries a fluid containing particles, e.g., including nanoparticles. In this example, the constriction structure 101 is configured as two aligned triangular needles each protruding from a base at opposite sides of the channel walls 105 to an apex near the center of the channel forming an opening between the needles. The opening can function as a constriction gap, e.g., which can be sized on the nanometer scale (e.g., in which the gap can be tens of nanometers wide, and in some examples, be 30 nm). The constriction structure 101 is formed of an electrically insulation material, which, in some implementations, can be the same material that forms the rest of the channel 102, e.g., including, but not limited to, glass, silica, oxidized silicon, silicon nitride, polysilsesquioxane (PSQ), polymethylmethacrylate (PMMA), polytetrafluoroethylene (Teflon), polyethylene, polyimide, polypropylene, polystyrene or other plastics, or a combination of at least some of these materials. In the exemplary device 100, no external electric field is present, nor fluidic flow, and thus the molecules 103 are shown to be diffused within the channel 102.

In FIG. 1A, the ac electric field applied along the channel 102 across the constriction structure 101 can be configured to generate a strong field gradient for the operation of positive dielectrophoresis if the dielectric permittivity of an analyte (e.g., such as the molecules 103) is larger than the dielectric permittivity of the medium (e.g., the fluid), or negative dielectrophoresis if the dielectric permittivity of the analyte is smaller than that of the medium. The PDEP creates an attractive potential that serves as a molecular trap, while the repulsive potential of the NDEP keeps molecules away from the nanoconstriction. However, when a dc bias is applied in the case of NDEP, for negatively charged particles, the applied energy tilts the repulsive potential into a slanted well, where the force balance condition (e.g., $F_{EP}=F_{EO}+F_{NDEP}$) occurs at local potential minimum, resulting in accumulation of the analyte in a continuous fashion, e.g., effectively working as a molecular dam.

The schematic 110 of FIG. 1A shows the channel 102 that includes the constriction structure 101 located within the channel carrying the fluid with the molecules 103 during the application of an ac electric field produced by an electrical energy source 114 configured to produce a PDEP effect. In the exemplary schematic 110, the applied electric field generated by the electrical energy source 114 becomes enhanced at the constriction structure 101 that effectively produces an attractive force that drives the molecules 103 to the nanoconstriction (e.g., particularly toward the constriction gap). An energy plot 119 shows that under PDEP conditions, particles in a fluid (e.g., the molecules 103) move toward a region or area in which they exhibit a minimum potential energy, which exists at the constriction gap. The PDEP technique can effectively create a molecular trap in adjacent regions on both sides of the constriction structure 101.

The schematic 120 of FIG. 1A shows the channel 102 that includes the constriction structure 101 located within the channel carrying the fluid with the molecules 103 during the application of an ac electric field produced by an electrical energy source 124 configured to produce an NDEP effect. In the exemplary schematic 120, the applied electric field generated by the electrical energy source 124 becomes enhanced at the constriction structure 101 that effectively produces a repulsive force that drives the molecules 103 away from the nanoconstriction. An energy plot 129 shows that under NDEP conditions, particles in a fluid exhibit a maximum potential energy at the constriction gap, e.g., which are dispersed away from the nanoconstriction.

The schematic 130 of FIG. 1A shows the channel 102 that includes the constriction structure 101 located within the channel carrying the fluid with the molecules 103 during the application of an ac electric field with a dc bias produced by an electrical energy source 134 configured to produce an NDEP+dc effect. In the exemplary schematic 130, the applied ac electric field generated by the electrical energy source 134 becomes enhanced at the constriction structure 101 that effectively produces a repulsive force that drives the molecules 103 away from the nanoconstriction. The applied dc bias generated by the electrical energy source 134 effectively produces an attractive force based on electrophoretic effects in a direction based on the opposite polarity to the net charge of the molecules 103. Additionally, electroosmotic forces effectively produce a repulsive force that drives the molecules 103 away from the nanoconstriction. For example, if the dc bias is applied with its negative terminal at the channel inlet shown on the left side of the schematic 130 and the net charge of the molecules 103 is negative, then the attractive EP force drives the molecules 103 to the nanoconstriction, which is opposed by the repulsive NDEP force and EO force. Or alternatively, for example, if the dc bias is applied with its positive terminal at the channel inlet shown on the left side of the schematic 130 and the net charge of the molecules 103 is positive, then the attractive EP force drives the molecules 103 to the nanoconstriction, which is opposed by the repulsive NDEP force and EO force. An energy plot 139 shows that under combined NDEP and EP conditions, particles in a fluid exhibit a maximum potential energy at the constriction gap, but exhibit a local minima near the constriction gap.

Figure 1B:
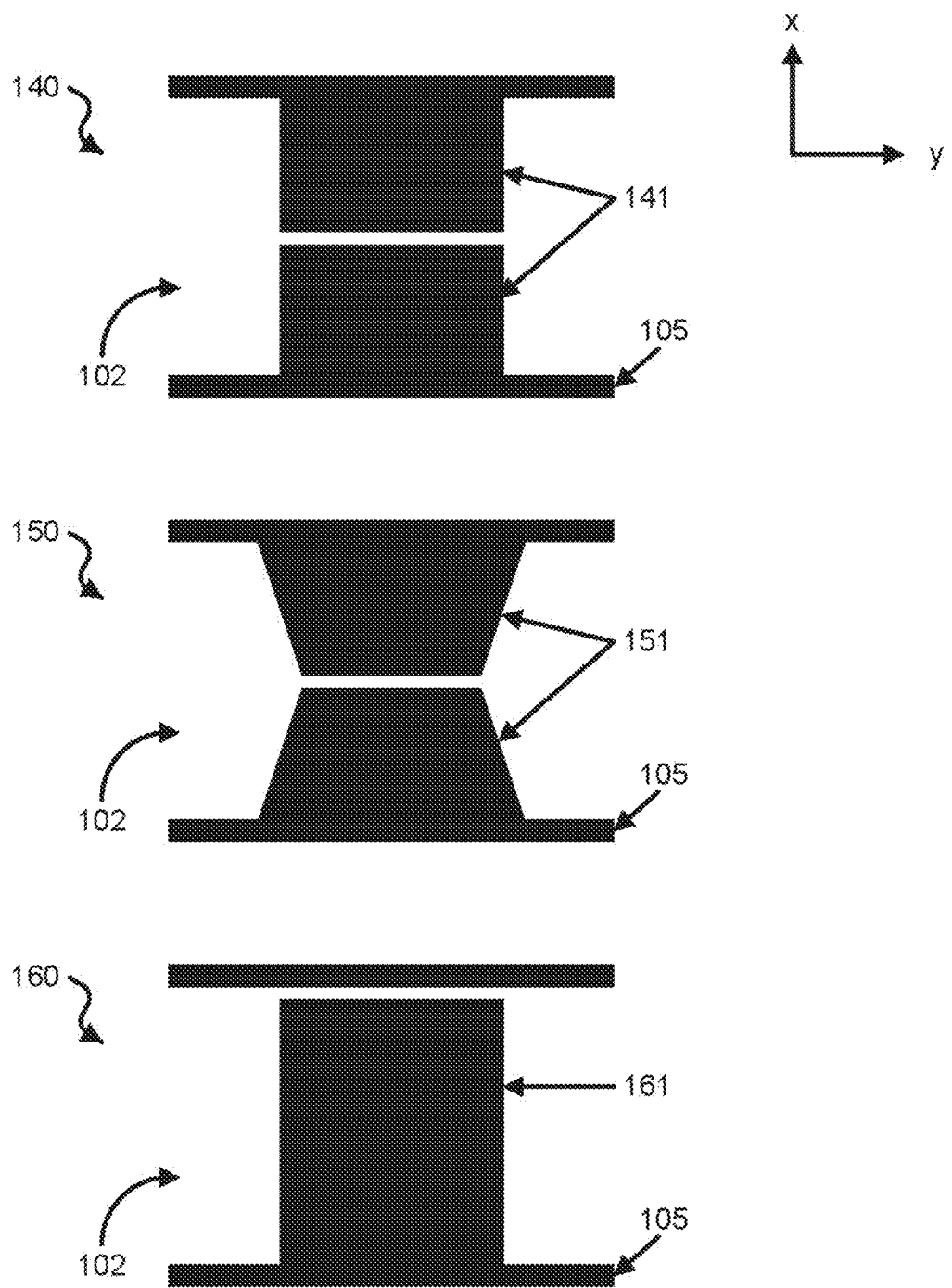
FIG. 1B shows schematics of other exemplary configurations of the constriction structure in the fluidic channel of exemplary devices of the disclosed technology.

FIG. 1B shows schematics of other exemplary configurations of the constriction structure in the fluidic channel of exemplary devices of the disclosed technology. The schematics of FIG. 1B show the top view of the constriction structures in the exemplary fluidic channels, e.g., in an x-y plane indicated by the exemplary orientation legend. In some implementations, for example, the schematics of FIG. 1B can also represent a cross-sectional side view of the constriction structures in the exemplary fluidic channels, e.g., in a y-z plane.

In one example shown in FIG. 1B, a schematic 140 shows the channel 102 including a constriction structure 141 configured as two parallel-aligned rectangular solids each protruding from a base at opposite sides of the channel walls 105 forming a nanosized subchannel with an opening in the center of the channel 102 between the rectangular solids. The long narrow subchannel formed between the rectangular solids can function as the constriction gap, e.g., which can be sized on the nanometer scale (e.g., in which the gap can be tens of nanometers wide, and in some examples, be 30 nm). The constriction structure 141 is formed of an electrically insulative material.

In another example shown in FIG. 1B, a schematic 150 shows the channel 102 including a constriction structure 151 configured as two parallel-aligned trapezoidal solids each protruding from a base at opposite sides of the channel walls 105 forming a nanosized subchannel with an opening in the center of the channel 102 between the trapezoidal solids. The long narrow subchannel formed between the trapezoidal solids can function as the constriction gap, e.g., which can be sized on the nanometer scale (e.g., in which the gap can be tens of nanometers wide, and in some examples, be 30 nm). The constriction structure 151 is formed of an electrically insulative material.

In another example shown in FIG. 1B, a schematic 160 shows the channel 102 including a constriction structure 161 configured as a single rectangular solid protruding from one wall of the channel walls 105 and forming a nanosized subchannel with an opening along the (other) wall of the channel 102. The long narrow subchannel formed by the single rectangular solid can function as the constriction gap, e.g., which can be sized on the nanometer scale (e.g., in which the gap can be tens of nanometers wide, and in some examples, be 30 nm). The constriction structure 161 is formed of an electrically insulative material.

FIGS. 2A-2G show schematic illustrations of an exemplary nanoscale eDEP device and images of the exemplary nanochannels containing arrayed nanoconstriction structures.

Figure 2A:
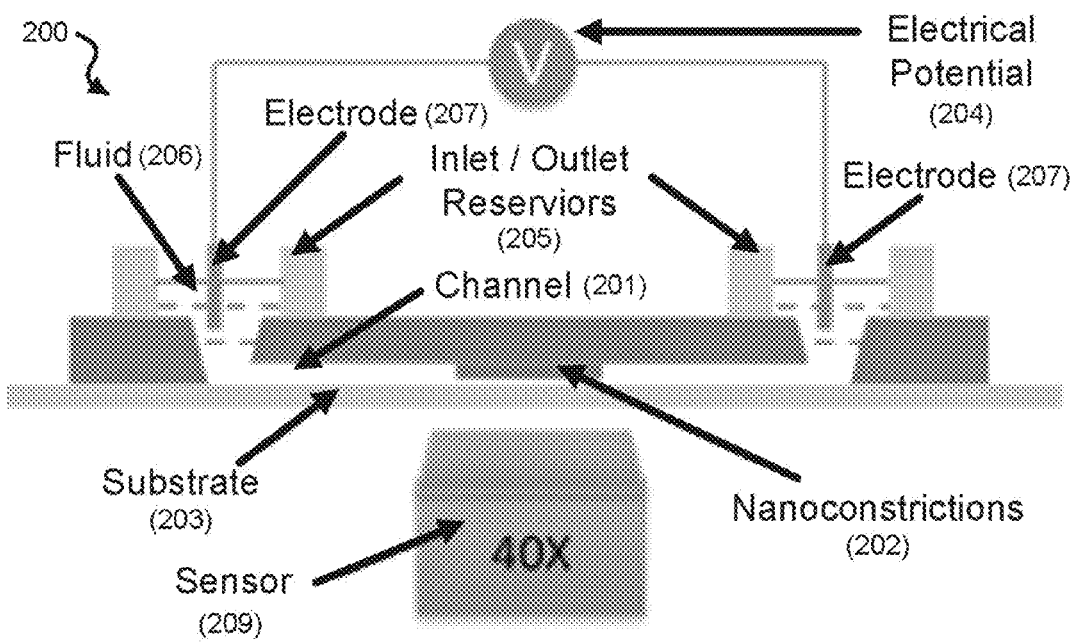
FIG. 2A shows a schematic of an exemplary nanoscale electrodeless dielectrophoresis (eDEP) device.

FIG. 2A shows a cross-sectional view of schematic of a nano eDEP device 200 that can be implemented for the operation of molecular damming to entrap and enrich small molecules, e.g., such as biomolecules, and particles. For example, the nano eDEP device 200 includes an electrically insulative substrate 203 with an insulative material layered on the substrate to form a channel 201 that carries an electrically conducting fluid 206 containing biomolecules. The channel 201 can be configured to have a microscale channel region leading to a nanochannel region, e.g., in which the nanochannel region of the channel 201 includes one or more nanoconstrictions 202. The nano eDEP device 200 can include inlet/outlet reservoirs 205 at the ends of the channel 201, e.g., which can be used to control the fluid 206 in the device 200. The device 200, or in some examples, a system that implements the device 200, can include an electrical energy source 204 providing an electrical potential, in which a non-uniform ac electric field with a dc bias can be applied along the channel 201. The electrical energy source 204 can be coupled to electrodes 207 at each end of the channel 201 that can be immersed in the fluid 206 through the inlet/outlet reservoirs 205 to provide the ac electric field and dc bias. For example, the electrical energy source 204 can be configured to apply an ac electric field with dc bias across the electrodes 207 to produce an NDEP+dc bias effect for molecular damming applications, e.g., based on the frequency of the applied electric field and the permittivity conditions of the biomolecules and the fluid. For example, for the fluid 206 including streptavidin proteins in a physiological buffer (e.g., 10 mM phosphate-buffered saline with 150 mM NaCl and 2 mM $NaN_3$, having a conductivity of 1.6 S/m), the device 200 can be configured to implement molecular damming of the streptavidin proteins in a region adjacent to the nanoconstrictions 202 in the channel 201 by applying a 214 $V_{pp}$/cm ac electric field with a frequency of 1 MHz with 1.5 V/cm dc bias using the electrical energy source 204. Also, for example, the electrical energy source 204 can be configured to create a PDEP effect for molecular trapping applications. For example, for the fluid 206 including the streptavidin proteins in the physiological buffer, the electrical energy source 204 can be configured to create a PDEP effect for molecular trapping in the nano eDEP device 200 by applying a 473 $V_{pp}$/cm ac electric field with a frequency of 10 kHz.

The exemplary nano eDEP device 200 can be operated with the applied dc bias having its negative terminal at one side of the channel 201, such that if the net charge of the molecules is negative, then the attractive EP force drives the molecules on the one side to the nanoconstriction 202, which is opposed by the repulsive NDEP force and EO force. For example, the molecules in this exemplary implementation can include proteins, which are mostly negatively charged in neutral buffers (e.g., pH=7). Proteins can also have no charge or positive charge, e.g., depending on its isoelectric point and the running buffer pH value. This degree of freedom can give rise to differential molecular entrapment and enrichment for molecular separation. For example, when mixed molecules are analyzed (e.g., such as different types of proteins or biomolecules), appropriate selections of electrical parameters can cause molecular separation of the mixed molecules based on their difference in polarizability and electrokinetic mobility, examples of which are described in subsequent sections.

The nano eDEP device 200 can include a sensor 209 to monitor or characterize the entrapped and enriched biomolecules in the collection region. The sensor 209 can be positioned in the molecular damming area, e.g., including under the channel (e.g., within or underneath the electrically insulating substrate 203) and/or along the side walls of the channel 201. In some examples, the sensor 209 can be an optical sensor, e.g., including an optical micrograph imager. For example, the exemplary optical micrograph imager can include an optical microscope or microscopy system, e.g., including, but not limited to, an inverted fluorescence microscope with a high magnifying objective lens (e.g., 40×) and an electron multiplying charge coupled device (EMCCD), or a Raman Spectroscopy microscope system. In other examples, the sensor 209 can include an electrical or electrochemical sensor (e.g., an electrode), a mechanical sensor, a magnetic sensor, or a sensing system. The sensor 209 can include a shape including, but not limited to, a wire or tube, a rectangular or triangular patch, a stripe, or a circular or elliptical dot. The sensor 209 can include an array of sensors configured in the exemplary shapes, e.g., an array of wires or tubes, an array of rectangular or triangular patches, an array of stripes, or an array of circular or elliptical dots. The sensor 209 can be configured to a size in the nanoscale or microscale, e.g., and as such can include nanowires. Additionally, or alternatively, for example, the nano eDEP device 200 can include a gating electrode configured in the enrichment zone that can be used to tune the electrical double layer (Debye layer) to locally control the electroosmotic flow, e.g., to further enhance enrichment. For example, the gating electrode can be embedded in a layer of insulating material, e.g., including the substrate, an additional electrically insulative layer configured within the channel, or in the insulative material that forms the channel. An electrical potential can be applied on the gating electrode that can affect the surface charge density in the channel (e.g., in the enrichment zone) that can affect the $F_{EO}$. For example, control of the $F_{EO}$ can allow alterations in the applied dc bias to adjust the $F_{EP}$, thereby providing further control to enrich the biomolecules in the nano eDEP device 200.

Figure 2C:
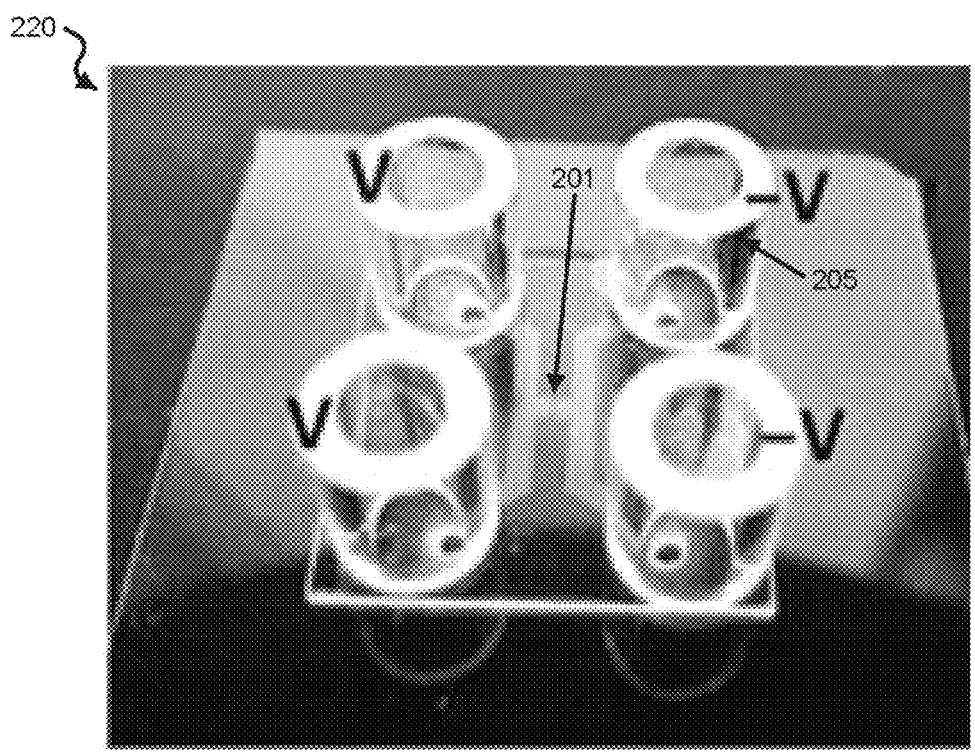
FIG. 2C show an image of the exemplary eDEP device.
Figure 2B:
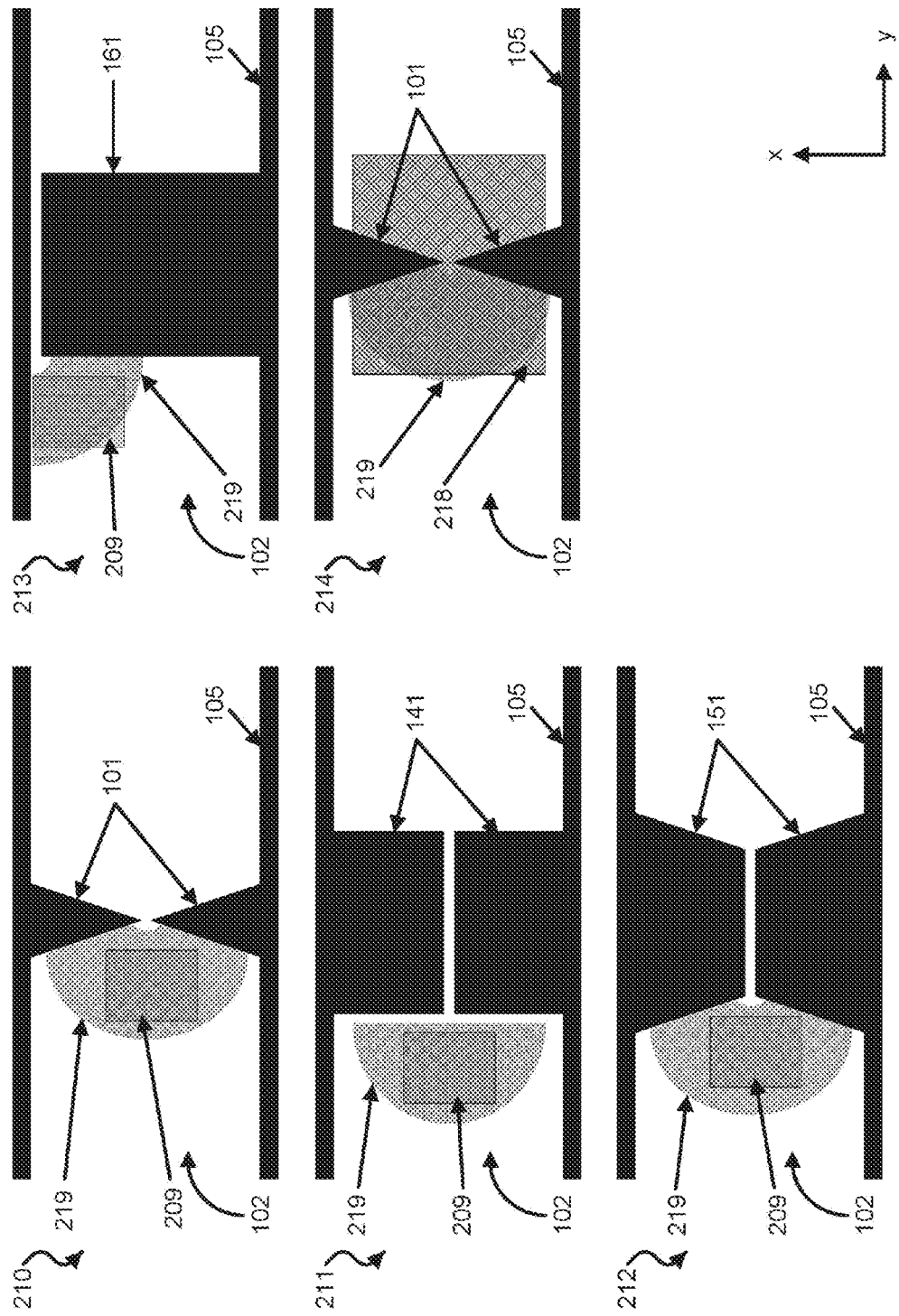
FIG. 2B shows schematics featuring various sensor configurations of exemplary eDEP devices.

FIG. 2B shows schematics featuring exemplary configurations of the sensor 209 positioned in the enrichment region of molecular damming by applying an ac electric field with dc bias using exemplary nano eDEP devices. The schematics of FIG. 2B show the top view of the constriction structures and sensors and/or gating electrodes in the exemplary fluidic channels, e.g., in an x-y plane indicated by the exemplary orientation legend. In some implementations, for example, the schematics of FIG. 2B can also represent a cross-sectional side view of the constriction structures and sensors in the exemplary fluidic channels, e.g., in a y-z plane.

In another example shown in FIG. 2B, a schematic 210 shows the channel 102 including the constriction structure 101 configured as two aligned triangular needles between the channel walls 105 forming an opening near the center of the channel. The opening can function as a constriction gap to magnify the applied electric field. In this example, the sensor 209 is positioned on one side of the constriction gap where an enrichment region 219 can be formed when an ac electric field with dc bias is applied, e.g., such that the polarity of the terminal of the dc bias applied on the side matches the net charge exhibited by the biomolecules in the fluid within the channel 102. In other examples, the sensor 209 can be placed on both sides of the constriction gap, e.g., which can be used in molecular trapping applications.

In another example shown in FIG. 2B, a schematic 211 shows the channel 102 including the constriction structure 141 configured as two parallel-aligned rectangular solids between the channel walls 105 forming a nanosized subchannel with an opening near the center of the channel. The long narrow subchannel formed between the rectangular solids can function as the constriction gap to magnify the applied electric field. In this example, the sensor 209 is positioned on one side of the constriction gap where the enrichment region 219 can be formed when an ac electric field with dc bias is applied, e.g., such that the polarity of the terminal of the dc bias applied on the side matches the net charge exhibited by the biomolecules in the fluid within the channel 102. In other examples of the schematic 211, the sensor 209 can be placed on both sides of the constriction gap, e.g., which can be used in molecular trapping applications.

In another example shown in FIG. 2B, a schematic 212 shows the channel 102 including the constriction structure 151 configured as two parallel-aligned trapezoidal solids between the channel walls 105 forming a nanosized subchannel with an opening near the center of the channel. The long narrow subchannel formed between the trapezoidal solids can function as the constriction gap to magnify the applied electric field. In this example, the sensor 209 is positioned on one side of the constriction gap where the enrichment region 219 can be formed when an ac electric field with dc bias is applied, e.g., such that the polarity of the terminal of the dc bias applied on the side matches the net charge exhibited by the biomolecules in the fluid within the channel 102. In other examples of the schematic 212, the sensor 209 can be placed on both sides of the constriction gap, e.g., which can be used in molecular trapping applications.

In another example shown in FIG. 2B, a schematic 213 shows the channel 102 including the constriction structure 161 configured as a single rectangular solid protruding from one wall of the channel walls 105 and forming a nanosized subchannel with an opening along the (other) wall of the channel 102. The long narrow subchannel formed by the single rectangular solid can function as the constriction gap to magnify the applied electric field. In this example, the sensor 209 is positioned on one side of the constriction gap where the enrichment region 219 can be formed when an ac electric field with dc bias is applied, e.g., such that the polarity of the terminal of the dc bias applied on the side matches the net charge exhibited by the biomolecules in the fluid within the channel 102. In other examples of the schematic 213, the sensor 209 can be placed on both sides of the constriction gap, e.g., which can be used in molecular trapping applications.

In another example shown in FIG. 2B, a schematic 214 shows the channel 102 including the constriction structure 101 forming the opening that can function as the constriction gap to magnify the applied electric field. A gating electrode 218 is positioned underneath the insulative layer of the substrate on the bottom of the channel 102 across the constriction gap. The gating electrode 218 can be configured under the enrichment region 219 and used to tune the electrical double layer (Debye layer) to locally control the electroosmotic flow, e.g., to further enhance enrichment. For example, by increasing the $F_{EO}$ by applying an electrical potential on the gating electrode 218 to alter the Debye layer, the enrichment region 219 can be made larger and enhance the enrichment process.

The nano eDEP device 200 can be configured with multiple inlet/outlet reservoirs 205 from which larger channels span to the channel 201, as shown in a photograph 220 of FIG. 2C. The photograph 220 shows an example of the device assembled on a 14×14 mm$^2$ substrate made of fused silica. For example, fused silica can be selected as the insulating substrate due to its robustness and low auto-fluorescence. The exemplary device in the photograph 220 includes four inlet/outlet reservoirs, e.g., two inlet/outlet reservoirs on each side of an H-shaped channel structure. The H-shaped channel structure includes multiple microscale channels that branch into nanochannels in the center of the "H" in between the microchannels, in which the nanochannels include the nanoconstrictions 202. For example, multiple reservoirs can be used to balance hydrostatic pressures in the channels and prevent any undesirable hydrostatic flow of the fluid. The microchannels of the exemplary device are configured to be 750 µm wide and 3 µm deep and are kept at an equal potential. For example, electrodes (e.g., four Au electrodes) can be inserted into the reservoirs to apply the electric field produced by the electrical potential source 204.

Figure 2D:
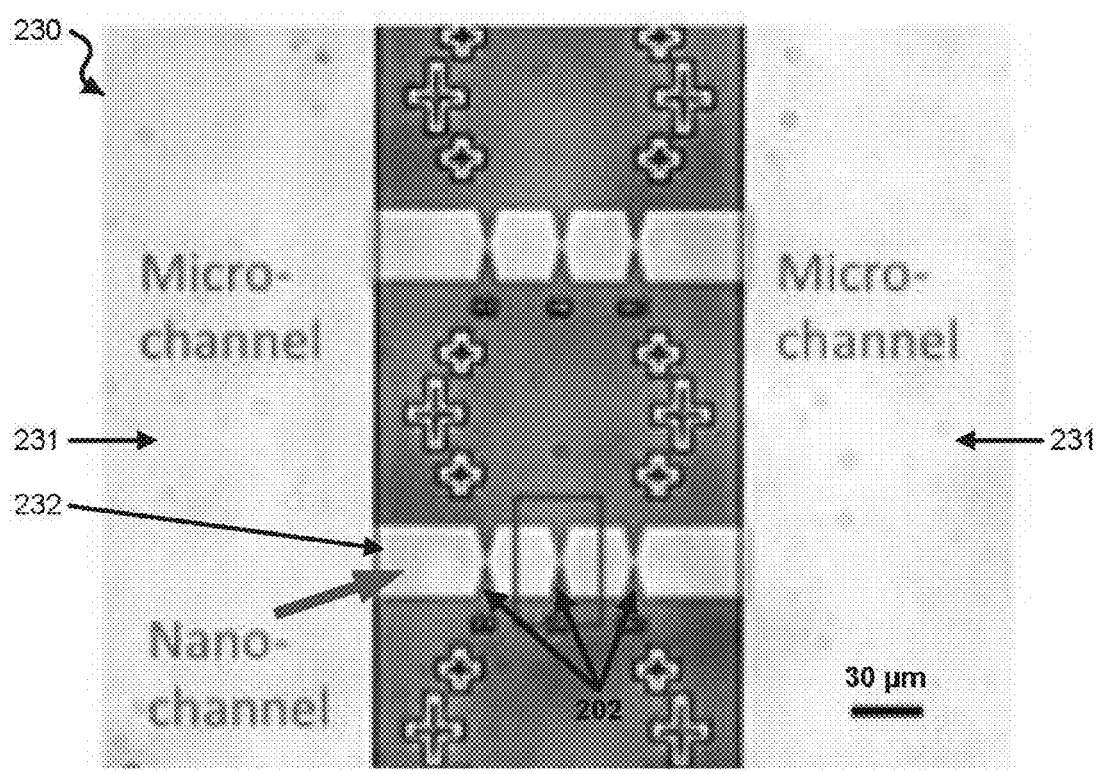
FIGS. 2D and 2E show images of the nanochannels containing arrayed nanoscale constriction structures of the exemplary eDEP device.
Figure 2E:
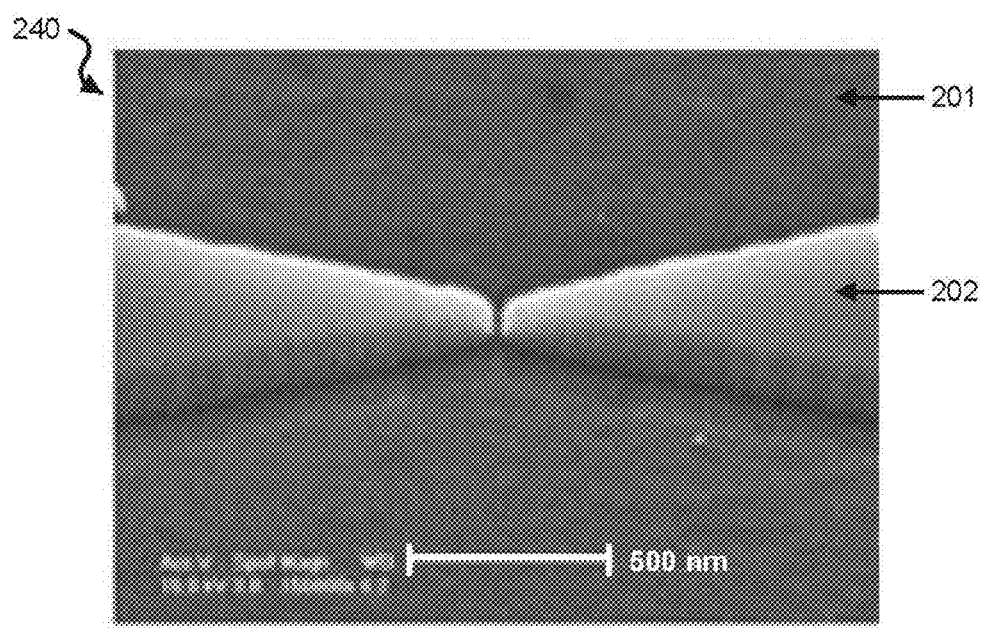

FIG. 2D shows an optical micrograph 230 that shows the center of the "H" in the H-shaped microchannel of the exemplary device (from FIG. 2C). The micrograph 230 shows two of the five nanochannels of the exemplary device, in which nanofluidic channels 232 are connected between the microfluidic channels 231. The nanochannels are configured to be 30 µm wide and 220 nm deep. Three nanoconstrictions 202 are seeded in each of the five exemplary nanochannels. FIG. 2E shows an SEM image of the boxed nanoconstriction (viewed in 90° turn, and 45° tilt) as shown in FIG. 2D with 30 nm gap size. The exemplary scale bar in FIG. 2D represents 30 µm, and 500 nm in FIG. 2E.

The described device can focus (or enhance) the displacement current in a conducting buffer through the reduction of cross-section of an insulating fluidic channel. Thus, the field-focusing factor in the described device can be determined. For example, if a microchannel with dimensions $X_{micro} \times Z_{micro}$ (width×height) is steeply reduced to a nanochannel of $X_{nano} \times Z_{nano}$ and the nanochannel is further reduced to a nanoconstriction of width $X_c$, a design rule for the overall field lens power of the described nano eDEP devices can be expressed as:

$$(X_{micro}/X_{nano}) \times (Z_{micro}/Z_{nano}) \times (X_{nano}/X_c)/n \qquad (3)$$

where n is the number of parallel nanochannels (e.g., n=5 in the exemplary device shown in FIGS. 2C and 2D), and provided the conductivity of the buffer remains substantially constant over all fluidic passages. This provision is valid in the described devices, as the Debye screening length (e.g., <1 nm) in the high-conductivity buffers used in the exemplary implementations described herein is much less than the nanoconstriction width and nanochannel height of the exemplary device. In the current exemplary design, the cross section of the microchannel is configured to be 750×3 (width×height) µm², and the cross section of the nanochannel is configured to be 30 µm×220 nm, with the nanoconstriction width configured to be 30 nm, and thus the overall field focusing factor is $\sim 7 \times 10^4 \times$. This exemplary field focusing factor leads to an enhancement factor of $\sim 5 \times 10^9$ for the dielectrophoretic force ($\sim E^2$) at the exemplary nano constrictions.

In some implementations, the nano eDEP device 200 can be operated to separate two or more particles from one another by producing differing field focusing factors at various nanoconstrictions 202 within the device 200 that effect the dissimilar particles differently. As described in Eq. (1), the $F_{DEP}$ on particles is size-, polarizability-, and electrical field gradient-dependent. In one example, the nano eDEP device 200 can be configured with a cascade of nanoconstrictions of various sizes (or, for example, shapes) that produce different electric field gradients based on the applied operating parameters of the device 200, thereby producing dielectrophoretic forces of differing strengths that can dam and separate the dissimilar particles at different nanoconstrictions along the cascade. For example, the operating parameters can include the frequency and/or amplitude of the electrical potential provided by the energy source 204 to apply the non-uniform ac electric field with a dc bias along the channel 201.

Figure 2F:
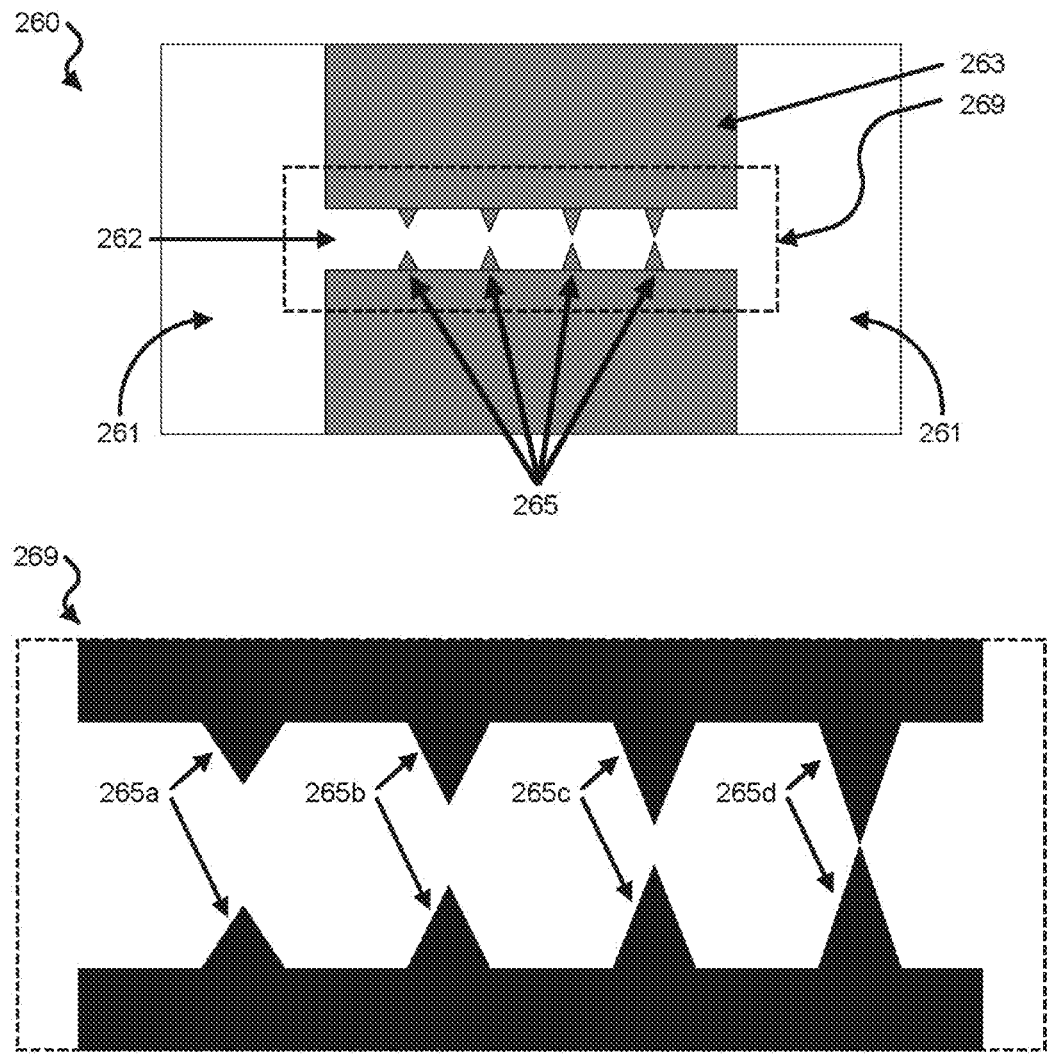
FIGS. 2F and 2G show schematics featuring various channel configurations of exemplary eDEP devices.

FIG. 2F shows a schematic of the center of a channel in an exemplary H-shaped micro-to-nano channel structure 260, which can be configured as the channel 201 of the exemplary device 200. The exemplary channel structure 260 includes two channel regions 261 (e.g., which can be configured as microscale channels) in which a smaller channel 262 (e.g., which can be configured as a nanoscale channel) is configured between the two channel regions 261. Electrically insulative material 263 is formed on the substrate 203 and structured to form smaller channel 262 between the two channel regions 261. An array or cascade of constriction structures 265 of varying sizes form openings of varying dimensions within the channel 262. FIG. 2F includes an inset schematic of a region 269 showing the constriction structures 265 cascaded as constriction structure 265a, 265b, 265c, and 265d structured to form a reduced opening size with respect to an adjacent constriction structure in one direction of the channel. For example, the constriction structure 265a forms a larger opening than that formed by 265b, etc., and thus the electric field gradient generated by constriction structure 265a is less than that of 265b, etc.

For example, a group of particles A and a group of particles B that vary in at least one of size, polarizability, or electrokinetic mobility from each other can be selectively isolated within the fluid by the constriction structures 265a, 265b, 265c, and 265d due to the differing strengths of the dielectrophoretic forces generated at each constriction structure based on the applied operating parameters. For example, if particles A have a greater size than particles B, then a lower electric field gradient is needed to produce the sufficient dielectrophoretic force to aggregate particles A to the constriction structure. Electrical parameters can be selected to produce sufficient $F_{DEP}$ (e.g., in the form of NDEP+dc) at the constriction structure 265a, for example, to aggregate the particles A. Based on the selected electrical parameters and the smaller size of particles B, in this example, the $F_{DEP}$ would not be sufficient to dam the particles B at the constriction structure 265a. The size of the nanoconstrictions can be configured such that the selected electrical parameters to dam particles A at constriction structure 265a, for example, are appropriate to produce the sufficient $F_{DEP}$ at the constriction structure 265d (or 265c or 265b) to aggregate the particles B. Thus, a chosen set of electrical parameters can lead to selective particle damming and enrichment of various types of particles using the exemplary device 200 with an array of size- or type-varying nanoconstrictions.

In another example, the nano eDEP device 200 can be configured with an array of nanochannels formed between two larger channels (e.g., such as the microchannels that connect with the inlet/outlet reservoirs 205 of the device 200), in which the array of nanochannels include differing sizes (e.g., channel width ($X_{nano}$) and/or channel height ($Z_{nano}$)) that produce different electric field gradients based on the applied operating parameters of the device 200, thereby producing dielectrophoretic forces of differing strengths that can dam and separate the dissimilar particles at different channels in the array.

Figure 2G:
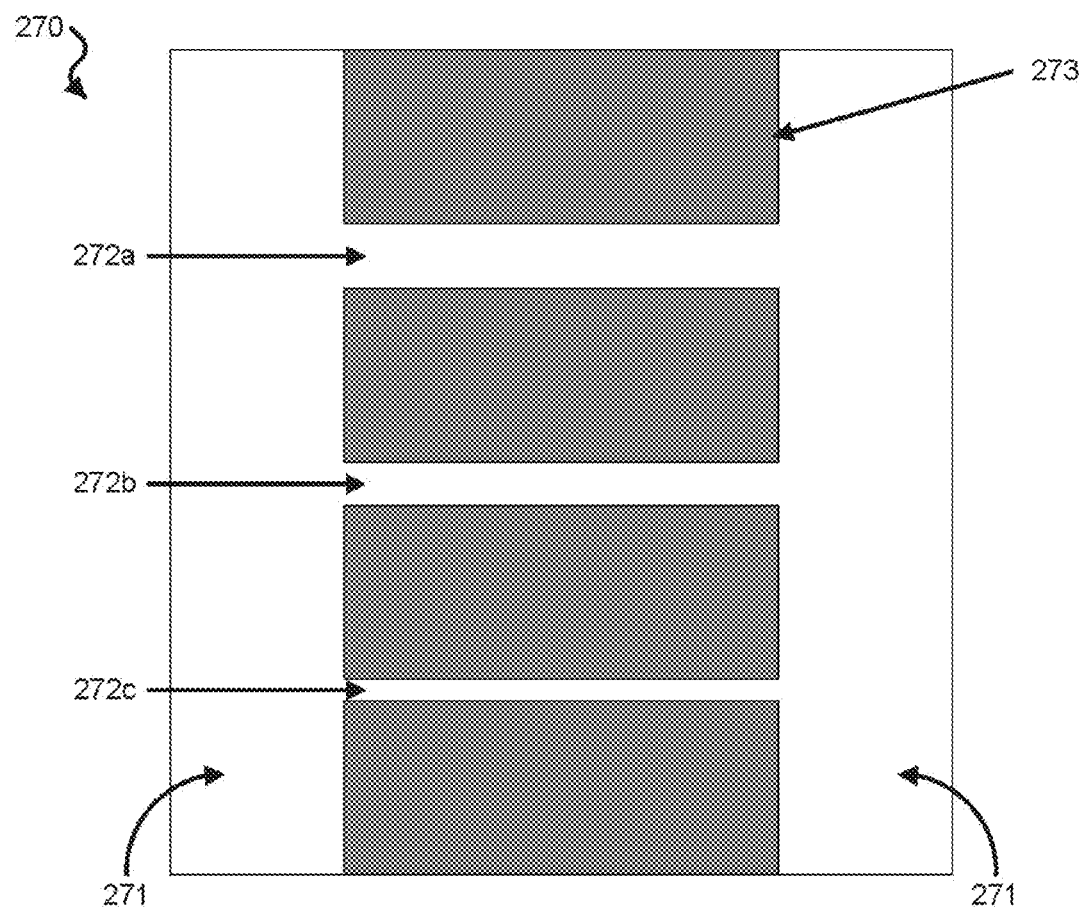

FIG. 2G shows a schematic of the center of an exemplary micro-to-nano channel structure 270, which can be configured as the channel 201 of the exemplary device 200. The exemplary channel structure 270 includes two channel regions 271 (e.g., which can be configured as microscale channels) in which an array of smaller channels 272a, 272b, and 272c (e.g., which can be configured as a nanoscale channel) is configured between the two channel regions 271. Electrically insulative material 273 is formed on the substrate 203 and structured to form the array of smaller channels 272a, 272b, and 272c between the two channel regions 271. Each channel of the array of smaller channels 272a, 272b, and 272c can be structured to include at least one different dimension with respect to the other channels of the array to form openings of the varying dimension(s) along the channel regions 271. For example, the channels 272a, 272b, and 272c shown in FIG. 2G are structured to form a reduced opening size with respect to an adjacent constriction structure in one direction along the channel regions 271. For example, the channel 272a forms a larger opening than that formed by 272b, etc., and thus the electric field gradient generated at the opening of the channel 272a is less than that of 272b, etc.

For example, the particles A and the particles B (e.g., which vary in at least one of size, polarizability, or electrokinetic mobility from each other) can be selectively isolated at the opening region of the nanochannels 272a, 272b, and 272c due to the differing strengths of the dielectrophoretic forces generated based on the applied operating parameters. For example, if particles A have a greater size than particles B, then a lower electric field gradient is needed to produce the sufficient dielectrophoretic force to aggregate particles A at the opening region of the nanochannels. Electrical parameters can be selected to produce sufficient $F_{DEP}$ (e.g., in the form of NDEP+dc) at the opening region of the nanochannel 272a, for example, to aggregate the particles A. Based on the selected electrical parameters and the smaller size of particles B, in this example, the $F_{DEP}$ would not be sufficient to dam the particles B at the nanochannel 272a. The size of the nanoconstrictions can be configured such that the selected electrical parameters to dam particles A at the opening region of the nanochannel 272a, for example, are appropriate to produce the sufficient $F_{DEP}$ at the opening region of the nanochannel 272a (or 272c) to aggregate the particles B. Thus, a chosen set of electrical parameters can lead to selective particle damming and enrichment of various types of particles using the exemplary device 200 with an array of size-varying nanochannels.

In these examples, a corresponding sensor 209 or gating electrode can be configured in the enrichment zone at each constriction structure of the array or cascade of constriction structures 265 or each channel of the array of channels 272a, 272b, and 272c. For example, the device 200 can be operated such that an electrical potential applied on the gating electrode that can affect the $F_{EO}$ in the enrichment zone and allow further control of the enrichment of the corresponding types of dammed particles (e.g., particles A or particles B).

In some implementations, the nano eDEP device 200 can be operated to separate two or more particles from one another by temporal control of the particle aggregation at the nanoconstrictions 202 (e.g., having a uniform field focusing factor at the nanoconstrictions) based on the control of the electrical parameters. For example, the device 200 can be configured using an exemplary design of the nanoconstriction structures, e.g., having a uniform type, spacing, size, etc. (e.g., such as constriction structures 101, 141, 151, 161 in FIGS. 1A and 1B, among other configurations), so that the group of particles A can be selectively isolated from particles B within the fluid at the nanoconstriction 202 in the channel 201 based on temporal factors to control the isolation and selection. For example, molecular damming of the particles A at the nanoconstriction 202 can occur faster than that of particles B, e.g., provided that particles A and B differ in at least one of size polarizability or electrokinetic mobility, for a given electric field gradient generated by constriction structure. Electrical parameters can be selected to produce an applied electric field, and the generated electric field can be applied for a particular duration, such that the particles A aggregate at the nanoconstriction 202 prior to particles B. The electric field can be paused or stopped, e.g., allowing collection of the separated and dammed particles A. Particles B can subsequently be dammed and collected at the nanoconstrictions after removal of particles A by applying the electric field for a longer duration to aggregate the particles B at the nanoconstriction 202.

In some implementations, at least one type of particles (e.g., target particles) among a plurality of types of particles to be separated by the device 200 can be configured with one or more capture probe particles (e.g., such as a nanoparticle with capture probes or capture probe molecule). For example, the capture probe particle can be conjugated or attached to the target particles to enhance the contrast of the target particles with respect to size (e.g., $r^3$ term of Eq. (1), which can further be varied based on different sizes of the attached nanoparticles), with respect to the CM factor (e.g., Re[K(ω)] term of Eq. (1)), and/or with respect to a fixed constriction geometry [e.g., $\nabla(E^2)$ term of Eq. (1)]. This can enhance the dielectrophoretic force contrast for separation of the types of particles.

Implementations of an embodiment of the disclosed nano eDEP device were performed to demonstrate protein enrichment by molecular damming effects and molecular trapping effects. For example, Alexa-488 labeled streptavidins (e.g., 52.8 kDa, 5 nm in diameter) in high-conductivity physiological buffers were used in some exemplary implementations. Results of the exemplary implementations showed that molecular damming can be implemented using the described device faster in seconds (e.g., 20 seconds in some implementations), which was shown to enrich proteins (e.g., increase the concentration) on the order of $10^5$ fold and be faster than the molecular trapping effect by orders of magnitude. Thus, for example, the exemplary device can be implemented as a sensing platform for rapid and sensitive protein analysis and biomarker discovery, as well as in precipitation study and protein crystallization and small molecules enrichment or screening applications.

Exemplary sample proteins used in the described implementations included Alexa-488 labeled streptavidins and goat anti-human IgG (Ga-HIgG) (e.g., 52.8 and 150 kDa, respectively, from Molecular Probes, Eugene, Oreg.). Alexa-488 streptavidins are circular and about 5 nm in diameter with a diffusion coefficient of 130 μm$^2$/s. Alexa-488 Ga-HIgG has a dimension of 14.5 nm×8.5 nm×4 nm. Alexa-488 has maximum excitation and emission have a wavelength at 495 and 519 nm, respectively. The buffer system used in the described implementations included 10 mM PBS (phosphate buffered saline) containing 150 mM NaCl and 2 mM NaN$_3$, pH 7.2, conductivity 1.6 S/m, e.g., which is similar to the physiological buffer conditions of the proteins. The exemplary imaging and electrical system used in the described implementations included an inverted epifluorescence microscope (IX 71, Olympus, Tokyo, Japan), equipped with a 40× objective (e.g., N.A. 0.7) and a thermoelectrically cooled electron multiplying charge coupled device (EMCCD) (iXonEM+888, Andor Technology, Belfast, Northern Ireland), which was used for fluorescence imaging of the molecular trapping and damming process. AC electric field was applied by a function generator (Agilent Technologies, Santa Clara, Calif.), coupled with a high-voltage broadband linear amplifier (A400DI, FLC Electronics AB, Partille, Sweden), and constantly monitored by an oscilloscope.

Figure 3A:
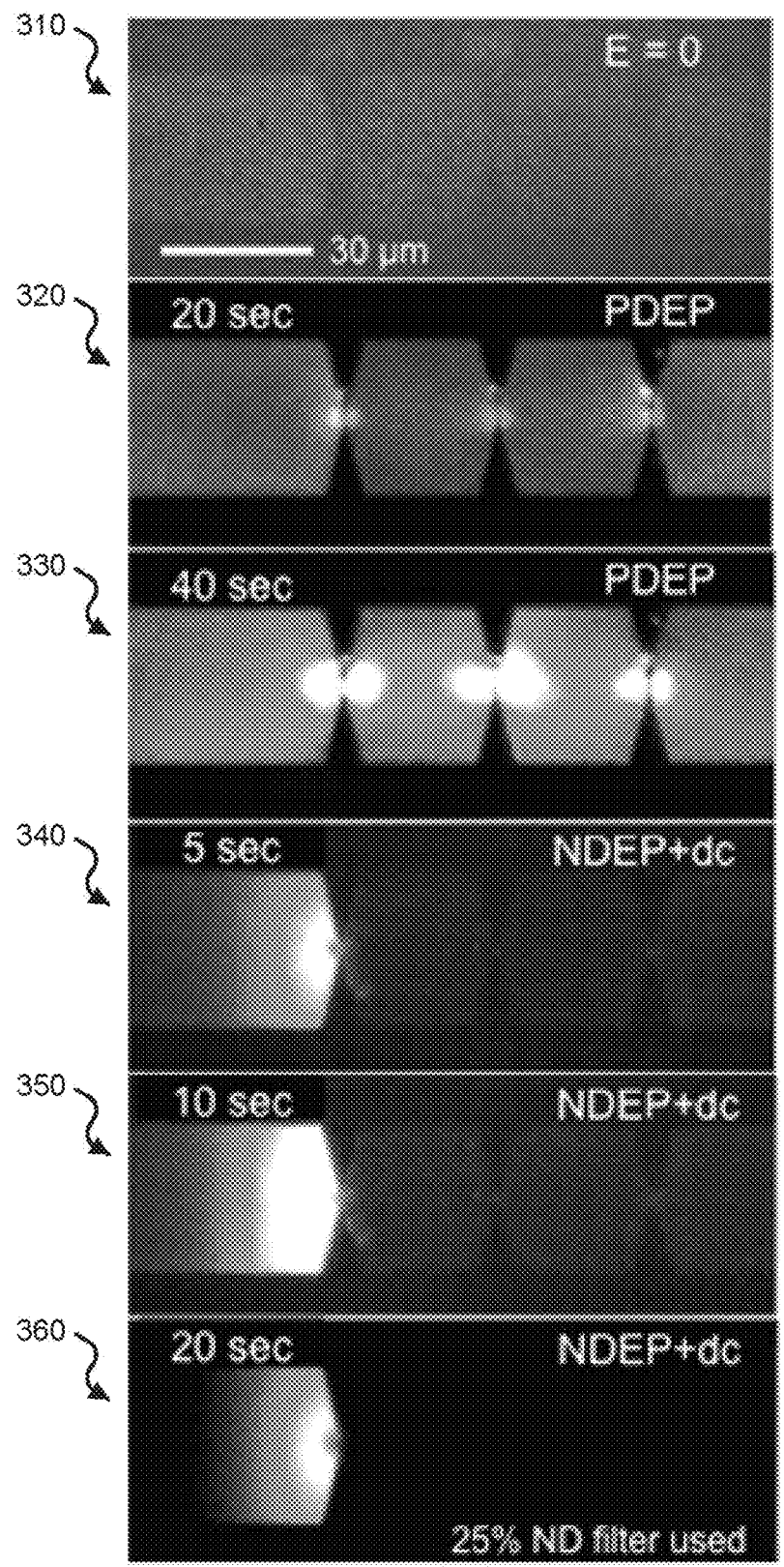
FIG. 3A shows images that demonstrate the protein trapping and damming functionalities of an exemplary eDEP device.

The exemplary implementations included loading an exemplary nano eDEP device with an initial concentration of 10 μg/mL Alexa-488 streptavidins and implementing PDEP and NDEP with dc biasing to compare the effectiveness of protein enrichment by trapping (PDEP) and damming (NDEP with dc bias). FIGS. 3A-3D show data that demonstrates the described protein trapping and damming functionality of the exemplary nanoscale eDEP device. FIG. 3A shows a data image 310 of proteins (e.g., Alexa-488 labeled streptavidins, 10 μg/mL) loaded in the chip by capillary force and without any applied electric field (E=0). As shown in the figure, no entrapment or damming is exhibited in the nanoconstrictions without an applied ac electric field. FIG. 3A shows data images 320 and 330 of the proteins trapped at nanoconstrictions after 20 s and 40 s, respectively, by implementing the PDEP functionality of the nano eDEP device after applying a 473 $V_{pp}$/cm ac field applied along the channel at 10 KHz. The electric field was focused $7\times10^4$ fold (e.g., ~$3.3\times10^9$ $V_{pp}$/m) over the applied field at the nanoconstrictions. All three nanoconstrictions shown in the images 320 and 330 exhibit molecular trapping of streptavidins through the implementation of PDEP using the exemplary device.

When the frequency was increased to ~1 MHz, the DEP can undergo a cross-over response from PDEP to NDEP with a changed sign of K(ω). FIG. 3A shows data images 340, 350, and 360 of the proteins dammed at nanoconstrictions after 5 s, 10 s, and 20 s, respectively, by implementing the NDEP+dc bias functionality of the nano eDEP device after applying a 214 $V_{pp}$/cm ac field at 1 MHz with 1.5 V/cm dc bias applied along the channel, e.g., with the positive potential at the right side of the channel. It is noted that in the data image 360, the image was recorded with a 25% transmittance neutral density (ND) filter to keep the intensity below the saturation of the EMCCD. For example, the dark zone at the center of the first constriction in the images 340, 350, and 360 indicates the NDEP mechanism that repels the streptavidin proteins away from the nanoconstriction gap. As shown in the images, virtually no excessive molecules go beyond the first dam for an effective accumulation at the second and third dams.

Figure 3B:
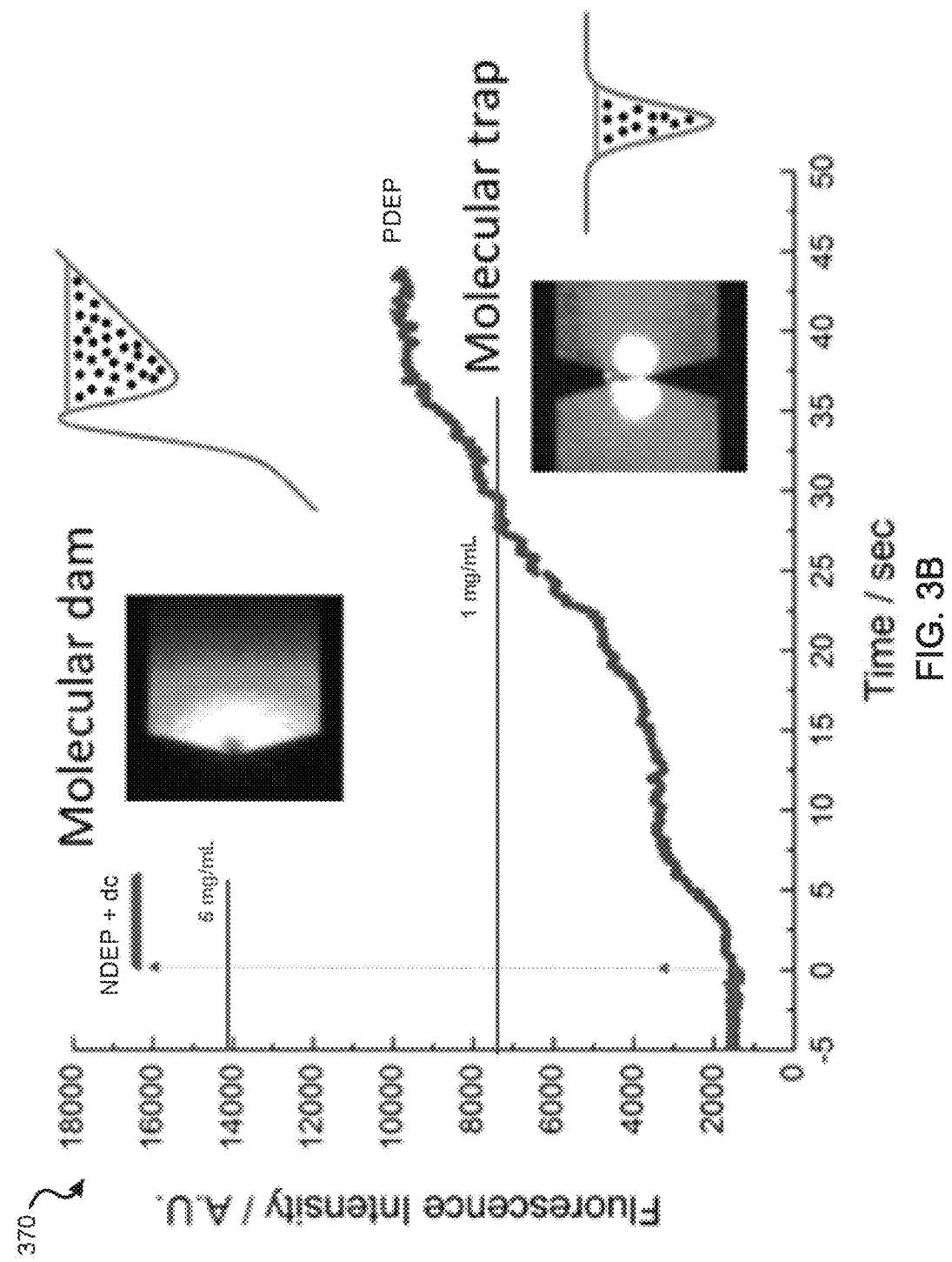
FIG. 3B shows an intensity plot of protein enrichment that demonstrates the molecular trapping and damming functionalities of the exemplary eDEP device.

FIG. 3B shows a data plot 370 of the corresponding intensity plot of protein enrichment, e.g., at an initial concentration of 10 μg/mL, operated under the same experimental conditions of molecular trapping and damming described above for the implementations shown in FIG. 3A. The data plot 370 includes a curve (NDEP+dc) demonstrating the results of the molecular damming functionality of the device and a curve (PDEP) demonstrating the results of the molecular trapping functionality of the device. The data plot 370 indicates that the damming effect is much more efficient in protein enrichment. For example, the NDEP+dc bias implementation demonstrated a $10^3$-fold concentration enhancement in 2-3 seconds after the electric field was turned on, as compared to the trapping effect of the PDEP implementation. The damming curve reached a plateau in the fluorescence intensity in the implementation, which meant the EMCCD had reached saturation, and thus an extended intensity plot with the use of ND filter is shown later in FIG. 3D.

The exemplary results suggest that operation of the nanoscale eDEP as a molecular dam (NDEP+dc) can be particularly advantageous for practical applications. For example, the NDEP+dc implementation was shown to be much more effective in protein enrichment than PDEP; potential Joule heating effects were alleviated by displacement of the molecular dam away from the hot spot, e.g., geometrical center of the nanoconstriction; and the sensing element can be placed microns away from the nanoconstriction, a task easily achievable by conventional fabrication means, e.g., including photolithography. These exemplary results suggest that the disclosed technology can circumvent great technical challenges to integrate biosensors with protein enrichment functionalities.

Figure 3C:
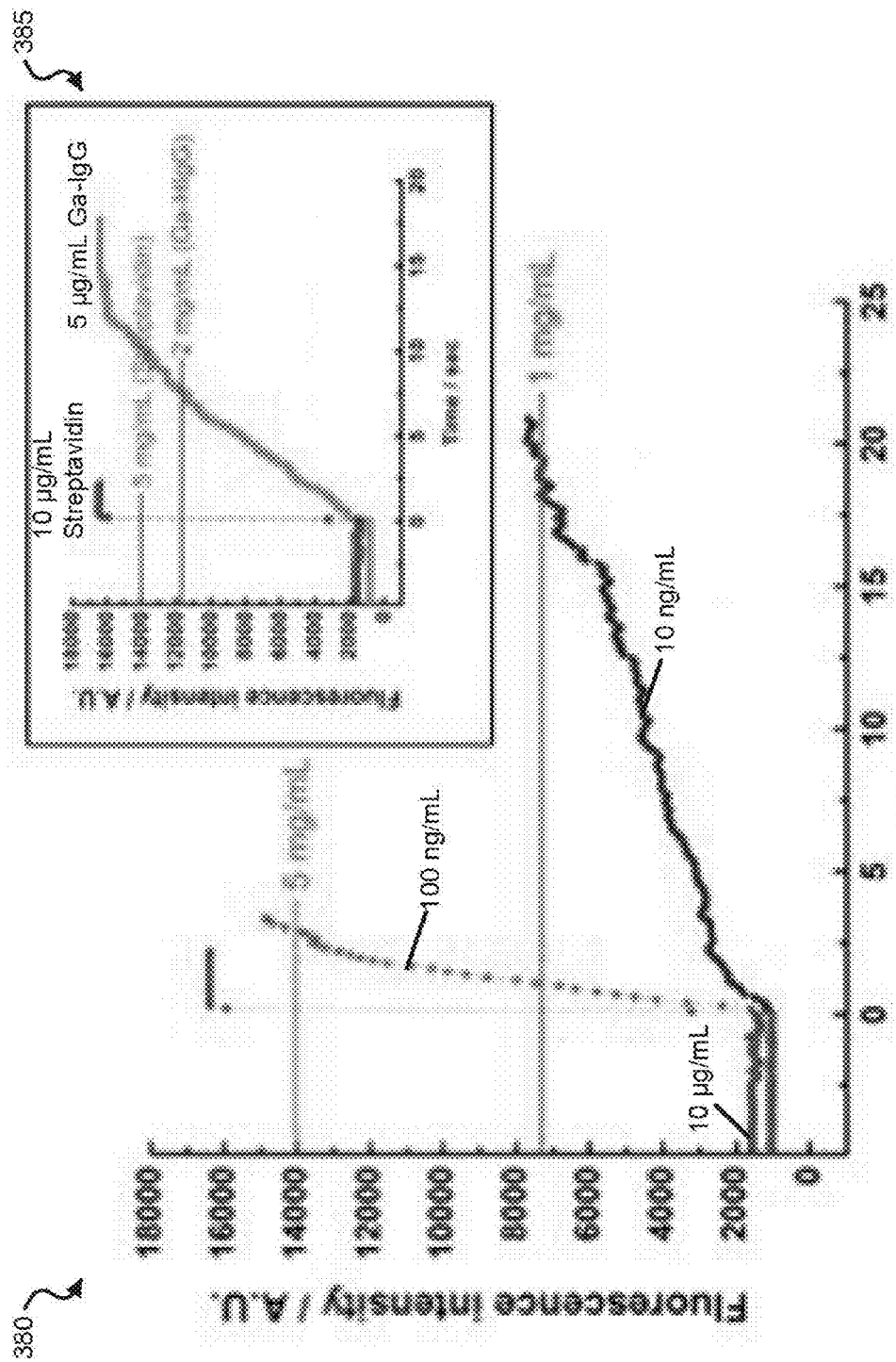
FIG. 3C shows a data plot of protein enrichment curves for various initial concentrations operated to implement molecular damming using the exemplary eDEP device.

FIG. 3C shows a data plot 380 of protein enrichment curves for various initial concentrations (e.g., 10 ng/mL or 189 pM, 100 ng/mL, and 10 μg/mL of streptavidin proteins) to further characterize the enrichment factors under molecular damming conditions, e.g., NDEP+dc bias (with corresponding dc bias of 1.5, 4.5, and 1.5 V/cm, respective to the initial concentrations). Exemplary concentration rulers of streptavidin are shown as horizontal lines to serve as references for calculating the enrichment factor and the time to reach the concentration rulers. As shown in the data plot 380, the 10 ng/mL proteins were enhanced >$10^5$ fold in less than 20 seconds, and 100 ng/mL and 10 μg/mL proteins were enhanced in under 5 s.

An inset plot 385 is shown in the data plot 380 of FIG. 3C showing the damming of Alexa-488 labeled goat anti-human IgG (e.g., ~150 kDa) in comparison to Alexa-488 streptavidins. The exemplary curves shown in the plot 385 shows a 400-fold enrichment in 7.5 s from a concentration of 5 μg/mL (33 nM) of Ga-HIgG and a 500-fold enrichment in <1 s of the Alexa-488 streptavidins under the same applied field conditions as in the data images 340, 350, and 360. The exemplary results demonstrate the effect of the molecular size and the polarizability for different proteins, e.g., indicating protein separation based on their difference in polarizability and electrokinetic mobility. In this example, separation of the dammed Alexa-488 labeled goat anti-human IgG from the dammed Alexa-488 streptavidins was performed using the exemplary nano eDEP device using temporal control of the particle aggregation at the nanoconstrictions for the selected set of electrical parameters used to generate the molecular damming (NDEP+dc) effect.

Figure 3D:
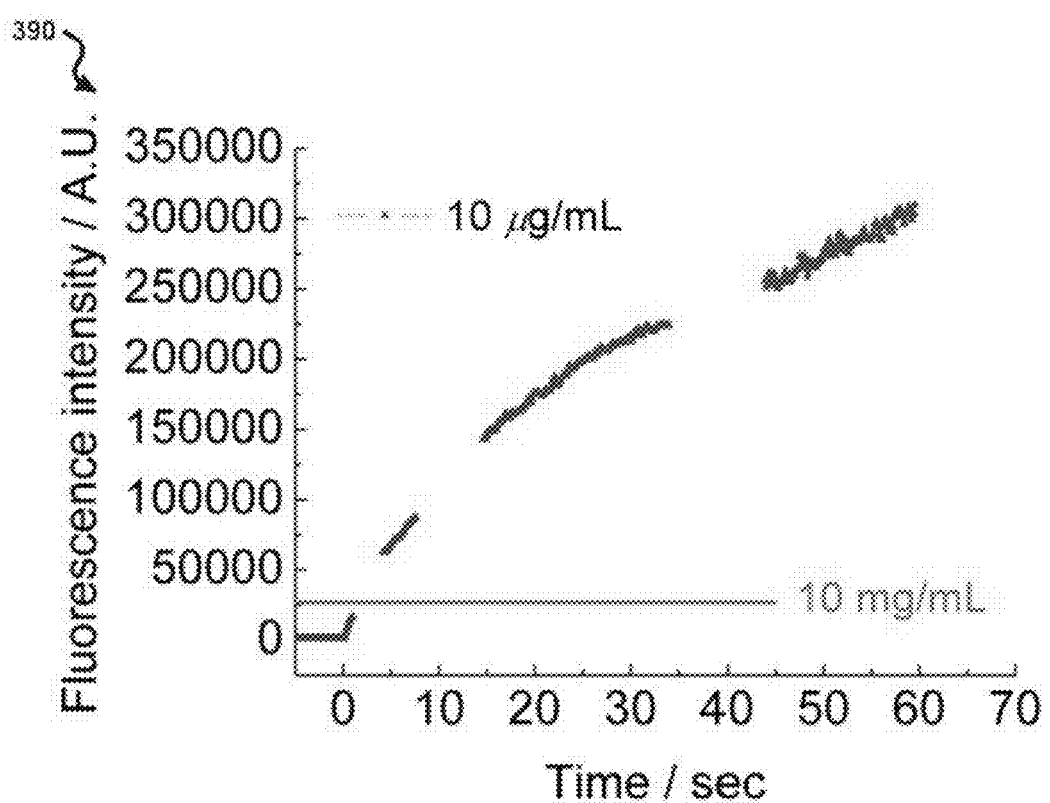
FIG. 3D shows a data plot of the enrichment of Alexa 488-streptavidins by the molecular damming effect.

FIG. 3D shows a data plot 390 showing the enrichment of Alexa 488-streptavidins by molecular damming effect at starting concentration of 10 μg/mL. For example, as shown in the figure, a $10^3$-fold concentration enhancement was achieved in 2-3 seconds. An exemplary concentration ruler of 10 mg/mL is shown in the figure as the horizontal line. The intensity discontinuities were caused by the time needed in switching the neutral density filters to prevent the saturation of EMCCD camera.

The exemplary data presented in the data plots 370, 380 and 390 of FIGS. 3B, 3C, and 3D, respectively, were plotted from the region of highest intensity of fluorescent signals (with an area of 9.6 μm² or 24 pixels) where proteins are mostly enriched, after subtracting the background from dark counts and autofluorescence from the substrate. Based on these exemplary results, protein enrichment factor of greater than $10^5$-fold may be achieved in just seconds by implementing the NDEP+dc functionality of the exemplary nano eDEP device. For example, the fast transport of molecules are due to the highly constricted field at the nanoconstriction, which may also benefit from, for example, the micro- to nanochannel junction design. For example, the streptavidin velocity was enhanced from ~1.5 μm/s in the microchannel (e.g., 1.5 V/cm applied dc bias and bulk mobility of streptavidin 0.8±0.9 μm-cm/V-s) to ~100 μm/s by a 70-fold field enhancement when entering into the nanochannel and, further to ~10-15 cm/s by another 1000-fold field enhancement from the junction to the nanoconstriction (e.g., ~45 μm distance). For example, the depth of the effective potential energy, $U_{min}$, involved in the damming process was estimated using Boltzmann distribution, $10^5$-fold concentration enrichment corresponding to $U_{min}$~-12 $k_B T$, where $k_B T$ is the thermal energy.

For example, to demonstrate that the balance of $F_{EO}$ and $F_{EP}$ alone cannot achieve the significant protein enrichment observed in the exemplary device, the case of a pure DC field (e.g., up to 4.5 V/cm) was implemented. The pure DC field example failed to demonstrate any discernible protein enrichment. For example, the results of the pure DC field exemplary implementation suggested that $F_{EP}$ is much higher than $F_{EO}$ in the exemplary nano eDEP device. For example, to further demonstrate the role of $F_{NDEP}$ in molecular damming, the AC field was turned off (but not the dc bias), and the results showed that the highly enriched proteins quickly diffused away, e.g., due to the established concentration gradient by the molecular dam. Thus, $F_{NDEP}$ was shown to be essential for the protein damming effect using the described device. Additionally, for example, these results indicate the significant enrichment shown in the exemplary implementations cannot be achieved solely from the balance of $F_{EO}$ and $F_{EP}$ within the dc bias range applied.

The exemplary implementations included investigating potential Joule heating effect at and around the nanoconstrictions. For example, potential Joule heating effect due to the highly focused field at the nanoconstrictions (e.g., total current of 25 µA, or 5 µA per nanochannel, in the exemplary nano eDEP device) were alleviated, e.g., by at least one notion of using a small sample volume (e.g., ~1 pL in each nanochannel), with 220 nm liquid layer in the nanochannels, used in the exemplary nano eDEP device. For example, heat dissipation through the substrate, as a bulk thermal bath, was very effective (e.g., based on finite-element multiphysics simulations). However, in some examples, water bubbling at the constriction may occur if a pure dc field over 100-200 V/cm is applied. Within our conditions described in the exemplary implementations, the proteins at the trap were not denatured, and the trapping events are reversible, and there is no denaturation-associated aggregation that occurs in implementing the device. Additionally, implementing the molecular damming operation of the device enriches proteins at a distance away from the highly focused field constrictions, as previously described and shown in FIG. 3A.

Figure 4:
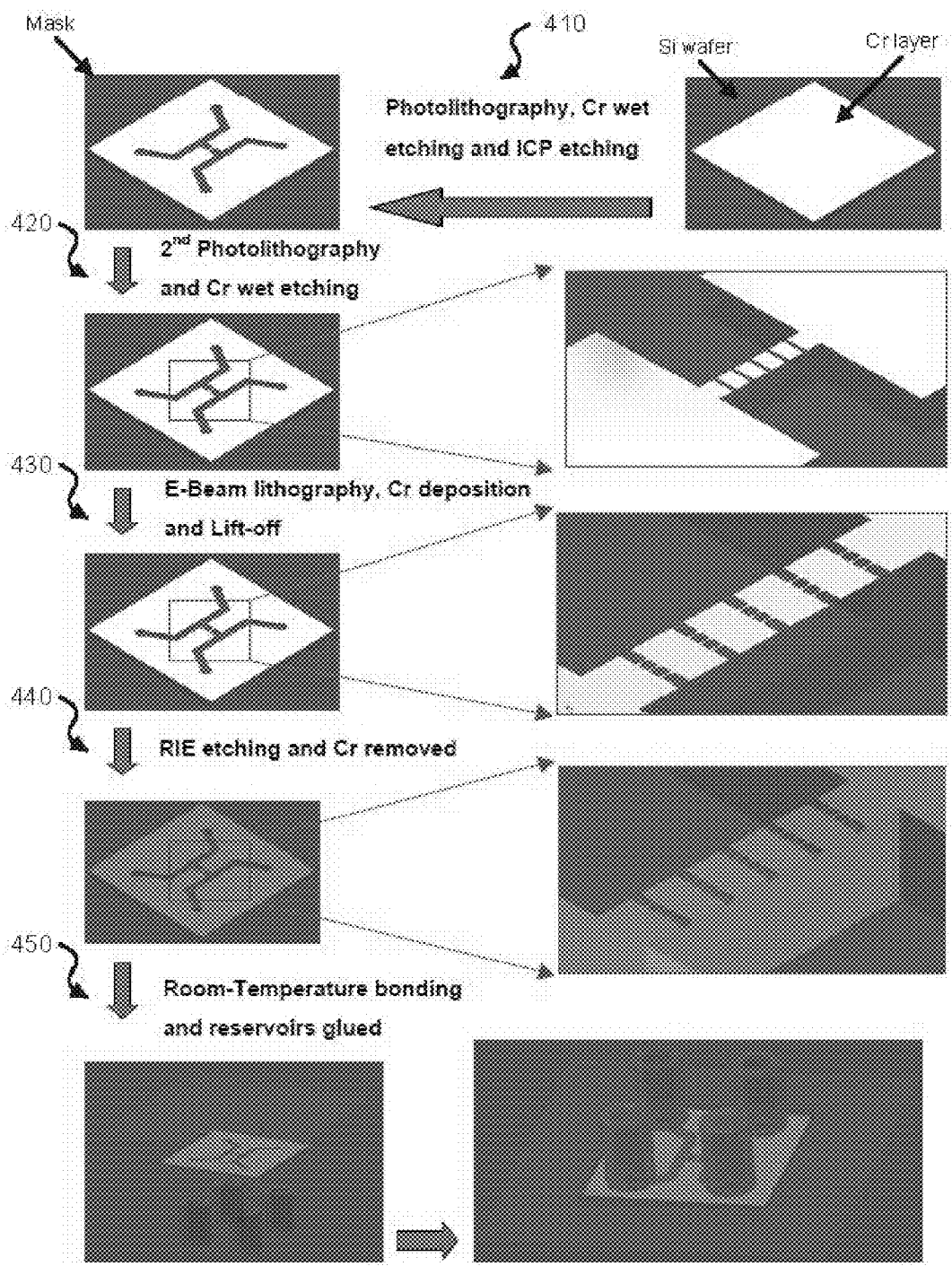
FIG. 4 shows a process diagram for the fabrication of exemplary nanoscale electrodeless dielectrophoresis devices.

FIG. 4 shows a process diagram for the fabrication of exemplary nanoscale electrodeless dielectrophoresis (nano eDEP) devices. A fabrication process of the exemplary devices can include a process 410 to define fluidic channels on a mask, e.g., by implementing photolithography and inductively coupled plasma (ICP) etching. For example, the fluidic channels can be defined in as H-shaped microchannels, which can be 750 µm wide and 3 µm deep. The process 410 can optionally include using piranha solution ($H_2SO_4$: $H_2O_2$=1:1) to clean a 4-inch fused silica wafer to remove organic contaminants before proceeding to subsequent processes, e.g., including photolithography and ICP etching. The process 410 can include, e.g., after the exemplary cleaning step, depositing a 30 nm thick Cr layer on the wafer followed by implementing resist coating, exposure, developing and Cr wet-etching steps to define a Cr etching mask. For example the Cr etching mask can be later used to pattern the exemplary 3-µm deep microfluidic channels by ICP etching. For example, the exemplary microchannels can be etched by ICP with a $CHF_3/CF_4/Ar/O_2$ mixture at bias/RF power 700/300 W for 3 min. The fabrication process can include a process 420 to fabricate nanochannels, e.g., by implementing a second photolithography and Cr wet etching. For example, the nanochannels can be configured from nanosized slit channels (e.g., which can be 30 µm wide and 220 nm deep). For example, the wafer can be diced, followed by the second photolithography process. The exemplary diced chips (e.g., which can be diced to a 14×14 mm² size) with microchannels can then be sand blasted, e.g., with a thick protective layer of photoresist to be removed later, to create inlet/outlet holes for reservoirs. For example, the exemplary loading holes can be created by sandblaster drilling through stainless steel mask from the backside of the device with the feature side protected by photoresist, which is later removed by acetone and cleaned by isopropanol. The process 420 can use the second photolithography process to pattern the 30 µm wide nanochannels in between the H-shaped microchannels. The fabrication process can include a process 430 to define the nanoconstrictions, e.g., by implementing electron beam lithography, along with another Cr deposition and lift-off process. For example, the 30 nm nanoconstrictions can be configured in nanochannels. The fabrication process can include a process 440 to create the depth of the nanochannel, e.g., by implementing reactive ion etching (RIE). For example, the exemplary nanochannels can be etched by RIE to form a 200 nm depth with a $CF_4/O_2$ mixture at 20 W for 10 min. For example, the etching depth and width for the microchannels can be measured by a surface profiler, and the nanochannels can be measured via white-light 3D surface profiler (e.g., Zygo, Middlefield, Conn., USA) and atomic force microscopy (e.g., Veeco, Plainview, N.Y.). The molecular traps with various constriction sizes were confirmed by scanning electron microscopy, as shown in FIG. 2E. The fabrication process can include a process 450 to assemble the device, e.g., by implementing a room-temperature and low-pressure sealing process. For example, a thin polysilsesquioxane (PSQ) film (e.g., ~100 nm thick), with high Young's modulus (e.g., ~800 MPa), can be spin coated at 3000 rpm onto a substrate (e.g., a piranha-cleaned glass coverslip) and baked for 30 min at 240° C. The PSQ can be diluted in xylenes to a 1:1.5 v/v ratio and filtered to remove particles. Then the exemplary silica substrate containing nanostructures and the PSQ-coated coverslip can be brought in contact, e.g., after 1 min high-pressure oxygen plasma treatment on both surfaces, to form permanent bonding caused by silanol condensation reaction. After the bonding step, quartz reservoirs can be epoxy-glued.

The multi-channel layout of the exemplary device can be used for parallel operation. In the described examples, miniaturization alleviates, rather than accentuates, the transport limitations so that essentially any sensor applications can be employed to capitalize on the ultrafast sample enrichment schemes described herein. Applications of the disclosed technology include entrapment (e.g., through the described damming techniques) and enrichment and characterization of any class of biomolecules, including, but not limited to proteins and single-stranded nucleic acids. Additionally, applications can also include DNA and RNA analysis, general protein assays, protein crystallization, rare biomarker discovery (e.g. coupled with mass spectroscopy), and early disease diagnostics in lab-on-a-chip systems, with extensions to small molecules (e.g. peptides or carbohydrates) enrichment or screening. The exemplary implementations demonstrated effective and efficient molecular damming effects using nanoconstriction-based eDEP, which is compatible with multiplexing and parallel analysis, as well as the use of high conductivity buffers, and thus suitable for the integration of biosensors.

Implementation of the disclosed biosensor devices can provide rapid enrichment of proteins on an order of at least $10^5$-fold enrichment (e.g., in 20 seconds). Exemplary devices can include the displacement of the molecular dam away from heating spots, e.g., geometrical center of the nanoconstriction, which can alleviate Joule heating effects. The described devices can be mass produced and fabricated using low-cost materials, e.g., including polymer or plastic, and can combine other sensor modalities including molecular filtering and detection on the same device platform. For example, the described devices can be mass-produced and fabricated by implementing hot embossing or (roll-to-roll) nanoimprinting techniques on polymers.

In another aspect, the disclosed technology includes a method to aggregate molecules in a fluid, e.g., using an exemplary embodiment of the nano eDEP device described herein. The method can include a process to receive an electrically conducting fluid containing molecules in a channel of the exemplary device formed of an electrically insulative material and having a constriction structure narrowing the channel width to form an opening with a size in the nanometer range. The method can include a process to select a frequency and magnitude of an ac electric field to be applied along the channel, e.g., in which the selection of the frequency of the ac electric field can determine the mode of operation of the device. For example, the frequency of the applied electric field can be at least one factor to determine if the constriction structure magnifies the applied ac electric field to produce a $F_{NDEP}$ in a direction away from the opening or a $F_{PDEP}$ in a direction toward the opening. The method can include a process to select a bias magnitude of a dc electrical signal to be applied along the channel. For example, the selection of the bias magnitude of the dc electric signal to a nonzero value can create an electrophoretic force in a direction toward the opening of the channel based on the polarity of the applied dc bias. For example, if the method is implementing an NDEP operation of the device (e.g., the frequency is selected to produce the $F_{NDEP}$), the produced electrophoretic force based on the selected dc bias magnitude can be used to drive the molecules toward an enrichment region on a side of the constriction structure. Thus, the method can include a process to apply the ac electric field and the dc bias along the channel to aggregate the molecules in a region near the opening.

The exemplary method can be implemented to aggregate biomolecules using an exemplary nano eDEP device of the disclosed technology in a variety of applications including general protein assays, protein crystallization, protein precipitation, rare biomarker discovery (e.g. coupled with mass spectroscopy), early disease diagnostics, small molecules (e.g. peptides or carbohydrates) enrichment or screening. In some examples, the method can further include a process to detect a parameter of the aggregated biomolecules using a sensor configured along the channel. For example, the process to detect the parameter can include acquiring an optical micrograph including data comprising illumination intensity of the aggregated biomolecules, e.g., in the cases in which the sensor includes an optical micrograph imager.

In another aspect, the disclosed technology includes a system to characterize molecules, e.g., such as biomolecules, and particles. The system can include an electrodeless dielectrophoresis chip, e.g., such as the nano eDEP device 200. For example, the electrodeless dielectrophoresis chip can include a substrate that is electrically insulating, a channel formed on the substrate structured to carry an electrically conducting fluid containing biomolecules, a constriction structure of an electrically insulative material configured in the channel to narrow the width of the channel and forming an opening with a size in the nanometer range, two microchannels formed of the electrically insulative material and having a channel width in a micrometer range, in which the channel is located between and connected to the two microchannels, and fluidic reservoirs located along the two microchannels. The system can include an electrical energy source that generates an ac electric field with a dc bias along the channel across electrode terminals configured within the fluidic reservoirs and in contact with the fluid, in which the constriction structure magnifies the applied ac electric field to produce a negative dielectrophoretic force ($F_{NDEP}$) in a direction away from the opening, and the applied ac electric field with the dc bias produces an electroosmotic force ($F_{EO}$) in the direction away from the opening and an electrophoretic force ($F_{EP}$) in a direction toward the opening, such that the $F_{NDEP}$, $F_{EO}$, and $F_{EP}$ combine to aggregate the biomolecules in an adjacent region (e.g., a molecular damming area) on a side of the opening. The system can include a characterization unit including a sensor positioned along the channel to detect a parameter of the aggregated biomolecules and a processing unit to process the detected parameter as data to determine a characteristic of the biomolecules.

For example, the sensor can be positioned in the molecular damming area. In some examples, the sensor can be an optical sensor, e.g., including an optical micrograph imager. In other examples, the sensor can include an electrical or electrochemical sensor (e.g., an electrode), a mechanical sensor, a magnetic sensor, or a sensing system. The sensor can, for example, include a shape including, but not limited to, a wire or tube, a rectangular or triangular patch, a stripe, or a circular or elliptical dot. The sensor can, for example, include an array of sensors configured in the exemplary shapes, e.g., an array of wires or tubes, an array of rectangular or triangular patches, an array of stripes, or an array of circular or elliptical dots. For example, the processing unit can include at least one processor (e.g., a microprocessor) and at least one memory that is in communication with the processor. The memory can, for example, include processor executable code, which when executed by the processor, configures the processing unit to perform various operations, such as receiving information, commands, and/or data, processing information and data, and transmitting or providing information/data to another entity or to a user.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for operating a device to aggregate particles in a fluid, comprising:

applying an ac electric field and a dc bias electric field along a channel in a device which includes:

a substrate that is electrically insulating;

an electrically insulative material formed on the substrate and structured to form the channel to carry an electrically conducting fluid containing particles; and a constriction structure formed of the electrically insulative material and located in the channel to narrow a channel dimension and forming an opening with a size in the nanometer range; and controlling the applied ac electric field and the dc bias electric field based on a structure of the constriction structure to magnify the applied ac electric field to produce a negative dielectrophoretic force ($F_{NDEP}$) in a direction away from the opening to combine with an electroosmotic force ($F_{EO}$) that is caused by the applied ac electric field with the dc bias to be in the direction away from the opening to counter an electrophoretic force ($F_{EP}$) in a direction toward the opening so that the $F_{NDEP}$, $F_{EO}$, and $F_{EP}$ operate collectively to aggregate the particles in an adjacent region on a side of the opening.

2. The method of claim 1, wherein the electrically insulative material includes at least one of glass, silica, oxidized silicon, silicon nitride, polysilsesquioxane (PSQ), polymethylmethacrylate (PMMA), or plastic.

3. The method of claim 1, wherein the particles include at least one of proteins, nucleic acids (DNA or RNA), peptides, or carbohydrates.

4. The method of claim 3, wherein the proteins include a negative net charge and the adjacent region is on the negatively charged side of the dc bias.

5. The method of claim 1, further comprising a sensor located along the channel to detect a parameter of the aggregated particles.

6. The method of claim 5, wherein the sensor is an optical micrograph imager that detects an illumination intensity of the aggregated particles.

7. The method of claim 5, wherein the sensor includes at least one of an electrical sensor, an electrochemical sensor, a mechanical sensor, or a magnetic sensor.

8. The method of claim 1, wherein the circuit includes a gating electrode configured outside of an insulative layer provided by at least one of the channel or the substrate and located along the channel on a side of the constriction structure to provide an electrical charge used to affect the $F_{EO}$.

9. The method of claim 1, wherein the size of the opening is in a range of 5 to 500 nanometers.

10. The method of claim 1, wherein the channel dimension is in a range of 100 nanometers to 1000 micrometers.

11. The method of claim 1, wherein the channel dimension includes a width or a height.

12. The method of claim 11, further comprising a first feeder channel and a second feeder channel having a channel width in a micrometer range or greater and formed of the electrically insulative material structured to carry the electrically conducting fluid, wherein the channel is located between and connected to the first feeder channel and the second feeder channel.

13. The method of claim 12, further comprising fluidic reservoirs located along the first feeder channel and the second feeder channel and electrode terminals configured within the fluidic reservoirs and in contact with the fluid, wherein the ac electric field and the dc bias is applied along the channel across the electrode terminals.

14. The method of claim 12, wherein the constriction structure magnifies by a field focusing factor based on $(X_{micro}/X_{nano}) \times (Z_{micro}/Z_{nano}) \times (X_{nano}/X_c)$ N, wherein $X_{micro}$ is the width of the feeder channel, $X_{nano}$ is the width of the channel, $Z_{micro}$ is the height of the feeder channel, $Z_{nano}$ is the height of the channel, $X_c$ is the width of the constriction structure, and N is a number of channels aligned in parallel between the first and second feeder channel.

15. The method of claim 1, wherein the adjacent region is located away from heating spots caused by Joule effects.

16. The method of claim 1, wherein the particles include an attached probe particle that enhance contrast of the particles due to a change in the size or the CM factor of the particles or response to an electric field gradient at the constriction structure.

17. A method for operating a device to characterize particles, comprising:

operating an electrodeless dielectrophoresis chip to carry an electrically conducting fluid containing particles, the chip including:

a substrate that is electrically insulating and structured to define a channel to carry the electrically conducting fluid, a constriction structure of an electrically insulative material configured in the channel to narrow a dimension of the channel and forming an opening with a size in the nanometer range, two microchannels formed of the electrically insulative material and having a channel width in a micrometer range or greater, wherein the channel is located between and connected to the two microchannels, and fluidic reservoirs located along the two microchannels;

applying an ac electric field and a dc bias along the channel across electrode terminals configured within the fluidic reservoirs and in contact with the fluid to magnify the applied ac electric field to produce a negative dielectrophoretic force ($F_{NDEP}$) in a direction away from the opening;

controlling the applied ac electric field with the dc bias to produce an electroosmotic force ($F_{EO}$) in the direction away from the opening and an electrophoretic force ($F_{EP}$) in a direction toward the opening so that the $F_{NDEP}$, $F_{EO}$, and $F_{EP}$ combine to aggregate the particles in an adjacent region on a side of the opening; and operating a characterization unit including a sensor positioned along the channel to detect a parameter of the aggregated particles and a processing unit to process the detected parameter as data to determine a characteristic of the particles.

18. The method of claim 17, wherein the electrodeless dielectrophoresis chip further includes a gating electrode configured outside of an insulative layer provided by at least one of the channel or the substrate and located along the channel on a side of the constriction structure to provide an electrical charge used to affect the $F_{EO}$.

19. The method of claim 1, wherein the nanometer range size of the opening formed by the constriction structure in the channel is 30 nm or less.

20. The method of claim 1, wherein the constriction structure includes a height of 220 nm or less.

21. The method of claim 1, wherein the constriction structure includes a width of 30 nm or less.

22. The method of claim 1, wherein the device is operable to aggregate the particles in the adjacent region on the side of the opening away from a gap region in the opening of the constriction structure.

23. The method of claim 1, wherein the device is operable to aggregate the particles in the adjacent region on a single side of the opening of the constriction structure.

24. A method to operate a device to aggregate particles in a fluid, comprising:

applying an ac electric field and a dc bias electric field along a channel in a device which includes:
a substrate that is electrically insulating;
an electrically insulative material formed on the substrate and structured to form the channel to carry an electrically conducting fluid containing particles; and
a constriction structure formed of the electrically insulative material and located in the channel to narrow a channel dimension and forming an opening with a size of 30 nanometers or less, wherein the constriction structure includes a height of 220 nanometers or less, and the constriction structure includes a width of 30 nanometers or less; and
controlling the applied ac electric field and the dc bias electric field based on a structure of the constriction structure to magnify the applied ac electric field to produce a negative dielectrophoretic force ($F_{NDEP}$) in a direction away from the opening to combine with an electroosmotic force ($F_{EO}$) that is caused by the applied ac electric field with the dc bias to be in the direction away from the opening to counter an electrophoretic force ($F_{EP}$) in a direction toward the opening so that the $F_{NDEP}$, $F_{EO}$, and $F_{EP}$ operate collectively to aggregate the particles in an adjacent region on a side of the opening.

25. The method of claim 24, wherein the electrically insulative material includes at least one of glass, silica, oxidized silicon, silicon nitride, polysilsesquioxane (PSQ), polymethylmethacrylate (PMMA), or plastic.

26. The method of claim 24, wherein the particles include at least one of proteins, nucleic acids (DNA or RNA), peptides, or carbohydrates.

27. The method of claim 24, further comprising a sensor located along the channel to detect a parameter of the aggregated particles, wherein the sensor includes an optical micrograph imager, an electrical sensor, an electrochemical sensor, a mechanical sensor, or a magnetic sensor.

28. The method of claim 24, wherein the circuit includes a gating electrode configured outside of an insulative layer provided by at least one of the channel or the substrate and located along the channel on a side of the constriction structure to provide an electrical charge used to affect the $F_{EO}$.

29. The method of claim 24, wherein the channel dimension includes a width or a height.

30. The method of claim 24, wherein the device includes:
a first feeder channel and a second feeder channel having a channel width in a micrometer range or greater and formed of the electrically insulative material structured to carry the electrically conducting fluid, wherein the channel is located between and connected to the first feeder channel and the second feeder channel; and
fluidic reservoirs located along the first feeder channel and the second feeder channel and electrode terminals configured within the fluidic reservoirs and in contact with the fluid, wherein the ac electric field and the dc bias is applied along the channel across the electrode terminals, wherein the constriction structure magnifies by a field focusing factor based on $(X_{micro}/X_{nano}) \times (Z_{micro}/Z_{nano}) \times (X_{nano}/X_c)/N$, wherein $X_{micro}$ is the width of the feeder channel, $X_{nano}$ is the width of the channel, $Z_{micro}$ is the height of the feeder channel, $Z_{nano}$ is the height of the channel, $X_c$ is the width of the constriction structure, and N is a number of channels aligned in parallel between the first and second feeder channel.

31. The method of claim 24, wherein the particles include an attached probe particle that enhance contrast of the particles due to a change in the size or the Clausius-Mossotti (CM) factor of the particles or response to an electric field gradient at the constriction structure.

32. The method of claim 24, wherein the device is operable to aggregate the particles in the adjacent region on the side of the opening away from a gap region in the opening of the constriction structure.

33. A method to operate a device to aggregate particles in a fluid, comprising:
applying an ac electric field and a dc bias electric field along a channel in a device which includes
a substrate that is electrically insulating;
an electrically insulative material formed on the substrate and structured to form the channel to carry an electrically conducting fluid containing particles; and
a single constriction structure formed of the electrically insulative material and located in the channel to narrow a channel dimension and forming an opening with a size in the nanometer range; and
controlling the applied ac electric field and the dc bias electric field to magnify the applied ac electric field to produce a negative dielectrophoretic force ($F_{NDEP}$) in a direction away from the opening to combine with an electroosmotic force ($F_{EO}$) that is caused by the applied ac electric field with the dc bias to be in the direction away from the opening to counter an electrophoretic force ($F_{EP}$) in a direction toward the opening so that the $F_{NDEP}$, $F_{EO}$, and $F_{EP}$ operate collectively to aggregate the particles in an adjacent region on a side of the opening.

34. The method of claim 33, wherein the electrically insulative material includes at least one of glass, silica, oxidized silicon, silicon nitride, polysilsesquioxane (PSQ), polymethylmethacrylate (PMMA), or plastic.

35. The method of claim 33, wherein the particles include at least one of proteins, nucleic acids (DNA or RNA), peptides, or carbohydrates.

36. The method of claim 33, further comprising a sensor located along the channel to detect a parameter of the aggregated particles, wherein the sensor includes an optical micrograph imager, an electrical sensor, an electrochemical sensor, a mechanical sensor, or a magnetic sensor.

37. The method of claim 33, wherein the circuit includes a gating electrode configured outside of an insulative layer provided by at least one of the channel or the substrate and located along the channel on a side of the constriction structure to provide an electrical charge used to affect the $F_{EO}$.

38. The method of claim 33, wherein the channel dimension includes a width or a height.

39. The method of claim 33, wherein the device includes:
a first feeder channel and a second feeder channel having a channel width in a micrometer range or greater and formed of the electrically insulative material structured to carry the electrically conducting fluid, wherein the channel is located between and connected to the first feeder channel and the second feeder channel; and
fluidic reservoirs located along the first feeder channel and the second feeder channel and electrode terminals configured within the fluidic reservoirs and in contact with the fluid, wherein the ac electric field and the dc bias is applied along the channel across the electrode terminals, wherein the constriction structure magnifies by a field focusing factor based on $(X_{micro}/X_{nano}) \times (Z_{micro}/Z_{nano}) \times (X_{nano}/X_c)/N$, wherein $X_{micro}$ is the width of the feeder channel, $X_{nano}$ is the width of the channel, $Z_{micro}$ is the height of the feeder channel, $Z_{nano}$ is the height of the channel, $X_c$ is the width of the constriction structure, and N is a number of channels aligned in parallel between the first and second feeder channel.

40. The method of claim 33, wherein the particles include an attached probe particle that enhance contrast of the particles due to a change in the size or the Clausius-Mossotti (CM) factor of the particles or response to an electric field gradient at the constriction structure.

41. The method of claim 33, wherein the constriction structure includes a height of 220 nanometers or less, and the constriction structure includes a width of 30 nanometers or less, and wherein the nanometer range size of the opening formed by the constriction structure in the channel is 30 nm or less.

42. The method of claim 33, wherein the device is operable to aggregate the particles in the adjacent region on the side of the opening away from a gap region in the opening of the constriction structure.

\* \* \* \* \*